United States Patent
Johan et al.

(10) Patent No.: US 9,079,881 B2
(45) Date of Patent: Jul. 14, 2015

(54) POLYMORPH OF 1-(2-METHYL-4-(2,3,4,5-TETRAHYDRO-1-BENZAZEPIN-1-YLCARBONYL)BENZYL-CARBAMOYL)-L-PROLINE-$N,N$-DIMETHYLAMIDE

(75) Inventors: Kjellström Henrik Johan, Copenhagen (DK); Johansson Erik Björn, Malmö (SE); Vilhelmsen Thomas, Karlslunde (DK)

(73) Assignee: Vantia Limited, Southampton (GB)

( * ) Notice: Subject to any disclaimer, the term of this patent is extended or adjusted under 35 U.S.C. 154(b) by 297 days.

(21) Appl. No.: 13/637,873

(22) PCT Filed: Mar. 31, 2011

(86) PCT No.: PCT/GB2011/000500
§ 371 (c)(1),
(2), (4) Date: Apr. 30, 2013

(87) PCT Pub. No.: WO2011/121308
PCT Pub. Date: Oct. 6, 2011

(65) Prior Publication Data
US 2014/0296213 A1 Oct. 2, 2014

Related U.S. Application Data

(60) Provisional application No. 61/347,048, filed on May 21, 2010.

(30) Foreign Application Priority Data

Apr. 1, 2010 (GB) .................................. 1005623.2

(51) Int. Cl.
*A61K 31/55* (2006.01)
*C07D 403/02* (2006.01)
*C07D 403/12* (2006.01)
*C07D 409/12* (2006.01)

(52) U.S. Cl.
CPC ............ *C07D 403/12* (2013.01); *C07D 409/12* (2013.01)

(58) Field of Classification Search
CPC .............................. A61K 31/55; C07D 403/02
USPC ...................................... 514/213.01; 540/593
See application file for complete search history.

(56) References Cited

FOREIGN PATENT DOCUMENTS

| WO | WO 97/22591 | 6/1997 |
| WO | WO 99/06403 | 2/1999 |
| WO | WO 99/06409 | 2/1999 |
| WO | WO 00/46224 | 8/2000 |
| WO | WO 00/46225 | 8/2000 |
| WO | WO 00/46227 | 8/2000 |
| WO | WO 00/46228 | 8/2000 |
| WO | WO 01/49682 | 7/2001 |
| WO | WO 02/00626 | 1/2002 |

OTHER PUBLICATIONS

Alauddin et al., "Effect of Organic Additives on the Cloud Point of Triton X-100 Micelles", Journal of Applied Sciences, 2009, 9(12), 2301-2306.

Yea et al., "New Benzylureas as a Novel Series of Potent, Nonpeptidic Vasopressin V2 Receptor Agonists", J. Med. Chem., Oct. 2008, 51, 8124-8134.

*Primary Examiner* — Brenda Coleman
(74) *Attorney, Agent, or Firm* — Baker & Hostetler LLP

(57) ABSTRACT

The invention provides a new polymorph of 1-(2-methyl-4-(2,3,4,5-tetrahydro-1-benzazepin-1-ylcarbonyl)benzyl-carbamoyl)-L-proline-N,N-dimethylamide, pharmaceutical compositions containing it and its use in therapy.

13 Claims, 7 Drawing Sheets

Figure 1:
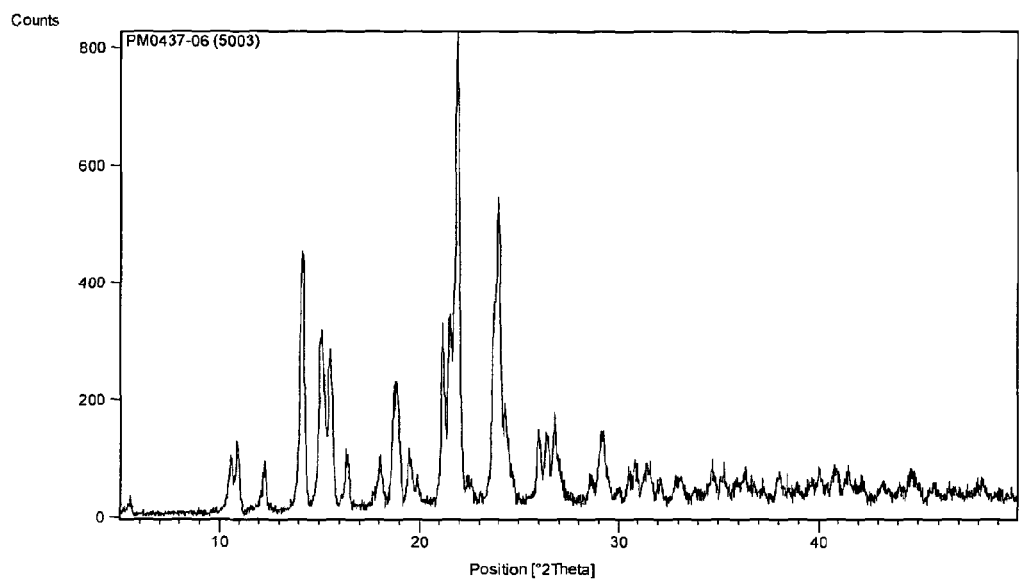

POLYMORPH OF 1-(2-METHYL-4-(2,3,4,5-TETRAHYDRO-1-BENZAZEPIN-1-YLCARBONYL)BENZYL-CARBAMOYL)-L-PROLINE-N,N-DIMETHYL-AMIDE

CROSS-REFERENCE TO RELATED APPLICATIONS

This application is the National Stage of International Application No. PCT/GB2011/000500, filed Mar. 31, 2011, which claims the benefit of Great Britain Application No. 1005623.2, filed Apr. 1, 2010, and U.S. Provisional Application No. 61/347,048, filed May 21, 2010, the disclosures of which are incorporated herein by reference in their entireties.

The present invention relates to a new polymorph of a vasopressin $V_2$ agonist, a pharmaceutical composition containing it and its use in therapy.

The neurophyseal hormones vasopressin (VP) and oxytocin (OT) are cyclic nonapeptides secreted by the posterior pituitary gland. Three subtypes of the VP receptor are known and these are designated the $V_{1a}$, $V_{1b}$ and $V_2$ receptors. Only one OT receptor has so far been well characterised.

The $V_{1a}$, $V_{1b}$, and $V_2$, as well as the OT receptors, are members of the super-family of seven transmembrane receptors known as G-protein coupled receptors. Vasopressin acts on the blood vessels, where it is a potent vasoconstrictor, and on the kidneys, where it promotes water reuptake leading to an antidiuretic effect. The cellular receptors that mediate these two actions have been characterised and shown to be different. The antidiuretic action is mediated by the type-2 vasopressin receptor, commonly called the $V_2$ receptor. Agents that can interact with the $V_2$ receptor and activate it in the same way as vasopressin are called $V_2$ receptor agonists (or simply $V_2$ agonists). Such agents will have an antidiuretic action. If these agents interact selectively with the $V_2$ receptor and not the other vasopressin receptor subtypes, then they will not have the hypertensive effect of vasopressin. This would be an important safety consideration and would make such agents attractive for the treatment of human disease conditions characterised by polyuria (which is herein taken to mean excessive urine production).

There exists a need for selective vasopressin $V_2$ receptor agonists that may be used in medicine. Both peptidic and non-peptidic $V_2$ agonists are known. An example of a peptidic $V_2$ agonist is desmopressin (also known as [1-desamino, D-Arg⁸], vasopressin, Minirin™, DDAVP™), which is a peptide analogue of vasopressin. Examples of non-peptidic vasopressin $V_2$ agonists are described in, for example, international patent applications WO 97/22591, WO 99/06403, WO 99/06409, WO 00/46224, WO 00/46225, WO 00/46227, WO 00/46228, WO 02/00626 and by Yea et al. in the *Journal of Medicinal Chemistry* (2008), 51(24), 8124-8134.

Besides its antidiuretic actions, desmopressin is used to increase the concentration in the blood of the coagulation proteins known as Factor VIII and von Willebrand factor. In the clinical context, this makes desmopressin useful in the treatment of haemophilia A and von Willebrand's disease. Similar applications would be open to other $V_2$ agonists.

In the manufacture of pharmaceutical formulations, it is important that the active compound be in a form in which it can be conveniently handled and processed in order to obtain a commercially viable manufacturing process. Accordingly, the chemical stability and the physical stability of the active compound are important factors. The active compound, and formulations containing it, must be capable of being effectively stored over appreciable periods of time, without exhibiting any significant change in the physico-chemical characteristics (e.g. chemical composition, density, hygroscopicity and solubility) of the active compound.

Furthermore, if the active compound is to be incorporated into a dosage form for oral administration, such as a tablet, it is desirable that the active compound be readily micronised to yield a powder with good flow properties to aid manufacture.

It is known that manufacturing a particular solid-state form of a pharmaceutical ingredient can affect many aspects of its solid state properties and offer advantages in aspects of solubility, dissolution rate, chemical stability, mechanical properties, technical feasibility, processability, pharmacokinetics and bioavailability. Some of these are described in "Handbook of Pharmaceutical Salts; Properties, Selection and Use", P. Heinrich Stahl, Camille G. Wermuth (Eds.) (Verlag Helvetica Chimica Acta, Zurich). Methods of manufacturing solid-state forms are also described in "Practical Process Research and Development", Neal G. Anderson (Academic Press, San Diego) and "Polymorphism: In the Pharmaceutical Industry", Rolf Hilfiker (Ed) (Wiley VCH). Polymorphism in pharmaceutical crystals is described in Byrn (Byrn, S. R., Pfeiffer, R. R., Stowell, J. G., "Solid-State Chemistry of Drugs", SSCI Inc., West Lafayette, Ind., 1999), Brittain, H. G., "Polymorphism in Pharmaceutical Solids", Marcel Dekker, Inc., New York, Basel, 1999) or Bernstein (Bernstein, J., "Polymorphism in Molecular Crystals", Oxford University Press, 2002).

International patent application WO 2001/049682 (PCT/GB2001/000023) describes a novel class of vasopressin agonists that display high, selective potency at the $V_2$ receptor. One such vasopressin agonist described in PCT/GB2001/000023 is 1-(2-methyl-4-(2,3,4,5-tetrahydro-1-benzazepin-1-ylcarbonyl)benzylcarbamoyl)-L-proline-N,N-dimethylamide [CAS 347887-36-9]. The preparation of 1-(2-methyl-4-(2,3,4,5-tetrahydro-1-benzazepin-1-ylcarbonyl) benzylcarbamoyl)-L-proline-N,N-dimethylamide described in PCT/GB2001/000023 yields an amorphous solid, which was found to be hygroscopic by Gravimetric Vapour Sorption Analysis (GVA).

Scanning electron micrographs (SEM) of this amorphous form show it to consist of irregular, predominantly large (>5 μm in diameter) aggregates. These properties of the amorphous form render it less suitable for use in a manufacturing process.

Various methods described in the known art (WO 2001/049682, WO 2002/000626 and in Yea et al, "New Benzylureas as a Novel Series of Potent, Non-peptidic Vasopressin V2 Receptor Agonists", Journal of Medicinal Chemistry (2008), 51(24), 8124-8134) have been applied to the synthesis of 1-(2-methyl-4-(2,3,4,5-tetrahydro-1-benzazepin-1-ylcarbonyl)benzylcarbamoyl)-L-proline-N,N-dimethylamide by the applicant but all have afforded an amorphous solid (known hereinafter as "the amorphous form"). In light of these investigations, it appeared extremely unlikely that a crystalline form of 1-(2-methyl-4-(2,3,4,5-tetrahydro-1-benzazepin-1-ylcarbonyl)benzylcarbamoyl)-L-proline-N,N-dimethylamide would ever be found.

Unexpectedly, however, it has now been found possible to prepare a stable, crystalline solid form of 1-(2-methyl-4-(2,3,4,5-tetrahydro-1-benzazepin-1-ylcarbonyl)benzylcarbamoyl)-L-proline-N,N-dimethylamide (known hereinafter as "the crystalline form"), which has advantageous physico-chemical properties, for example, with regard to chemical stability, hygroscopicity, processability, morphology and technical feasibility.

The process used for the preparation the crystalline form is unusual. When 1-(2-methyl-4-(2,3,4,5-tetrahydro-1-benzazepin-1-ylcarbonyl)benzylcarbamoyl)-L-proline-N,N-dimethylamide is dissolved in a solvent system from which it is to be crystallised, for example acetone/water, it displays unexpected and surprising behaviour, which would normally be associated with that of a non ionic surfactant. Non-ionic surfactant behaviour is typically observed in molecules which are surrounded by a hydrate shell at lower temperatures which allows for their complete solubility. An increase in temperature causes cleavage of the hydrogen bonds and the compound's solubility is rapidly decreased resulting in the compound separating out from the solution as an oil. Using surfactant terminology, this phase separation and sudden onset of turbidity when the temperature is raised is known as the "cloud point".

Despite the fact that the structure of 1-(2-methyl-4-(2,3,4,5-tetrahydro-1-benzazepin-1-ylcarbonyl)benzylcarbamoyl)-L-proline-N,N-dimethylamide is very different from well known non ionic surfactants, such as, for example, Triton X-100, a "cloud point" at approximately 38° C. is observed when a solution of 1-(2-methyl-4-(2,3,4,5-tetrahydro-1-benzazepin-1-ylcarbonyl)benzylcarbamoyl)-L-proline-N,N-dimethylamide in acetone/water (20/80) is heated. By analogy to surfactant precedent, but without being bound by any particular theory, a hydrate shell surrounding the compound would be anticipated below the cloud point and it is assumed that this increased order of molecular organisation would be an important structural prelude to crystallisation of the hydrate. The loss of the hydrated shell would encourage phase separation and loss of molecular organisation which would intuitively disfavour formation of the crystalline hydrate. This behaviour is unusual and would not be expected of a compound such as 1-(2-methyl-4-(2,3,4,5-tetrahydro-1-benzazepin-1-ylcarbonyl)benzylcarbamoyl)-L-proline-N,N-dimethylamide. The typical behaviour of non-ionic surfactants is described in publications such as M. Alauddin, T. Parvin & T. Begum, *Journal of Applied Sciences*, (2009), 9, 2301-2306; P. Huibers, D. Shah & A. Katritzky, *Journal of Colloid and Interface Science*, (1997), 193, 132-136; T. Inoue, H. Ohmura & D. Murata, *Journal of Colloid and Interface Science*, (2003), 258, 374-382; T. Iwanaga & H. Kunieday, *Journal of Colloid and Interface Science*, (2000), 227, 349-355; H. Schott, *Colloids and Surfaces A*, (2001), 186, 129-136; and D. Myers, 2005, Surfactant Science and Technology, 3rd Edition, Oxford University Press, New York, ISBN:978-0-471-68024-6.

A number of advantages associated with the crystalline form are described below.

SEM of the crystalline form shows it to have a regular, rectangular morphology. This consistent morphology allows for greater control of the manufacturing process and simpler tablet manufacturing. For example, tablets containing the crystalline form can be manufactured using a simple direct compression process. Attempts to manufacture tablets from the amorphous form were prone to failure.

Figure 7:
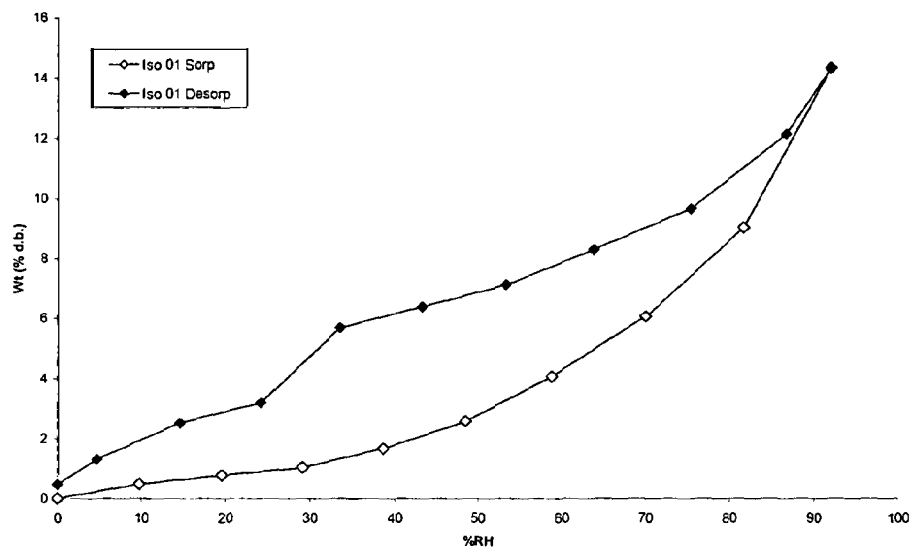
Figure 8:
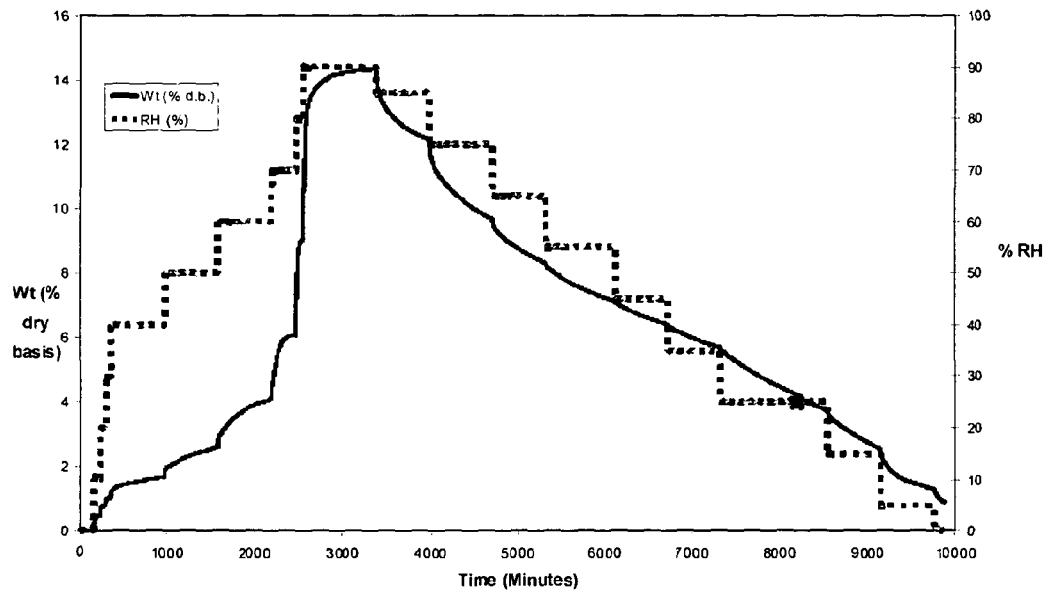
Figure 9:
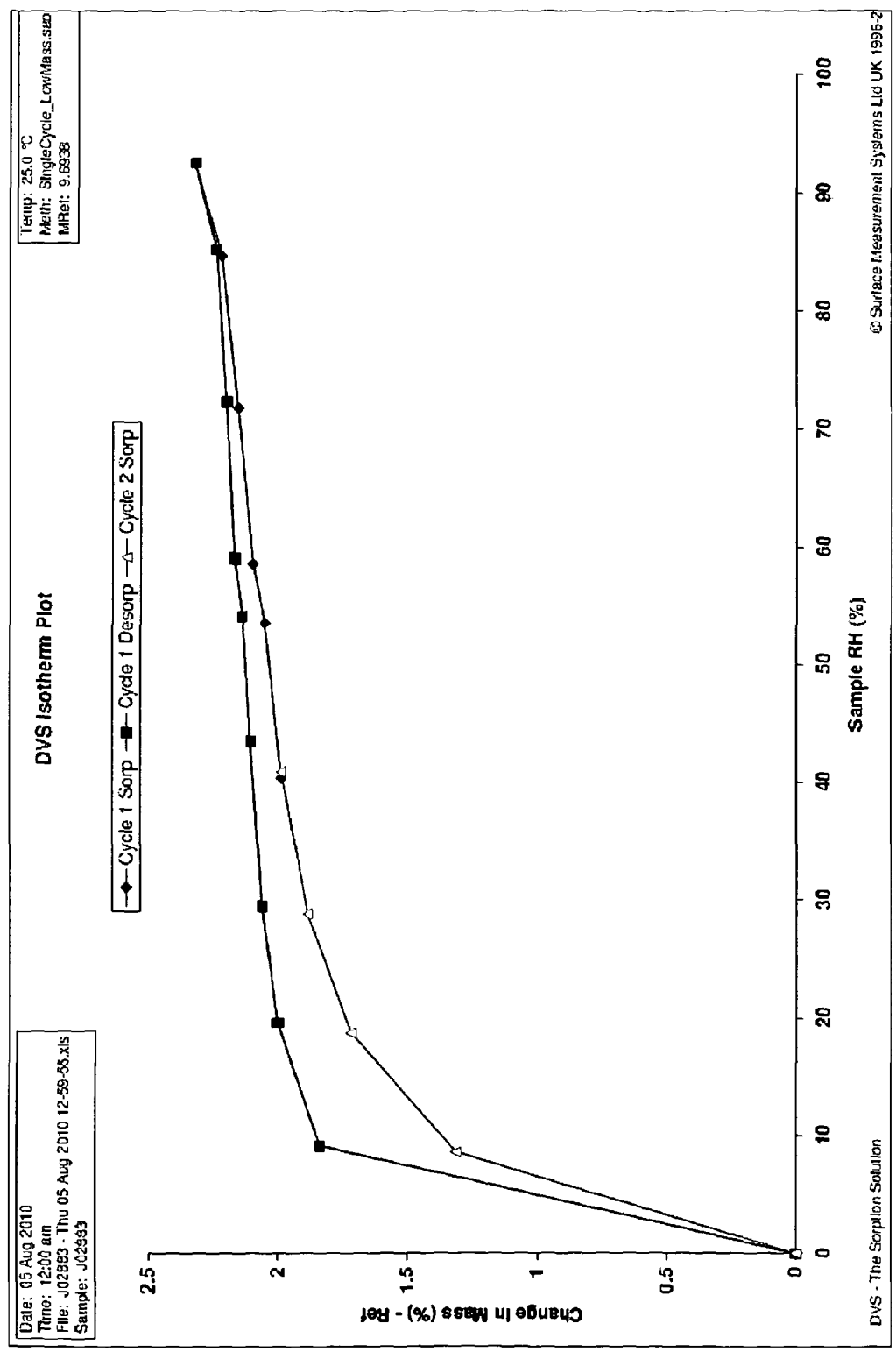
Figure 10:
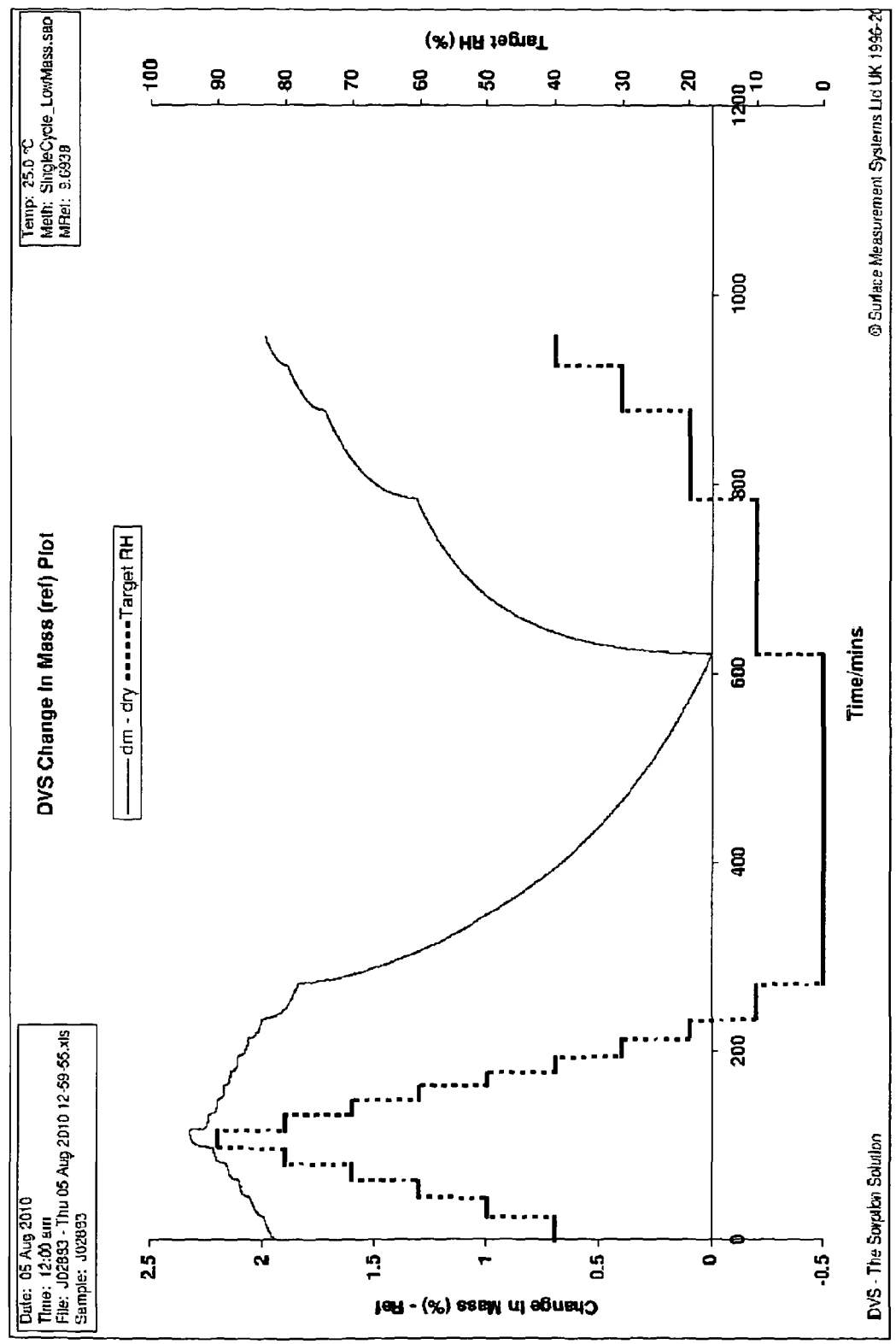

The crystalline form is, advantageously, much less hygroscopic than the amorphous form. FIG. 9 shows the GVA water sorption/desorption isotherm of the crystalline form and FIG. 10 shows the kinetic water sorption/desorption. These data show that there was no significant water uptake observed between 40% RH and 90% RH (approximately 0.3% w/w) by the crystalline form. Neither is there any change in solid form over the entire water sorption range. Analogous data in FIGS. 7 and 8 show that the amorphous form is highly hygroscopic absorbing water into the bulk of the sample upon storage above 30% RH (total of ca 14% at equilibration at 90% RH).

Further demonstration of the crystalline form's lack of hygroscopicity is shown by the stability data described below.

The crystalline form is more stable than the amorphous form. When both substances are stored for 6 months at 40° C. and 75% relative humidity the crystalline form remains as a white powder with no change in water content (3.8% according to Karl Fischer analysis). Also there is no significant degradation as measured by the sum of impurities which increases only from 0.9% to 1.0% (HPLC). However, the amorphous form became glassy in appearance and yellow in colour. It also showed increased moisture content, 5.7% from 1.3%, according to Karl Fischer analysis and faster degradation with increased amounts of impurities, 3.7% from 1.5% (HPLC).

The amorphous form has been found to entrap organic solvent, making it difficult to dry. This is a problem because if a compound contains too high a level of residual solvent, it may be rendered unsuitable for pharmaceutical use. In contrast, the crystalline form does not entrap organic solvent, meaning that it can be dried easily, using standard procedures.

Figure 11:
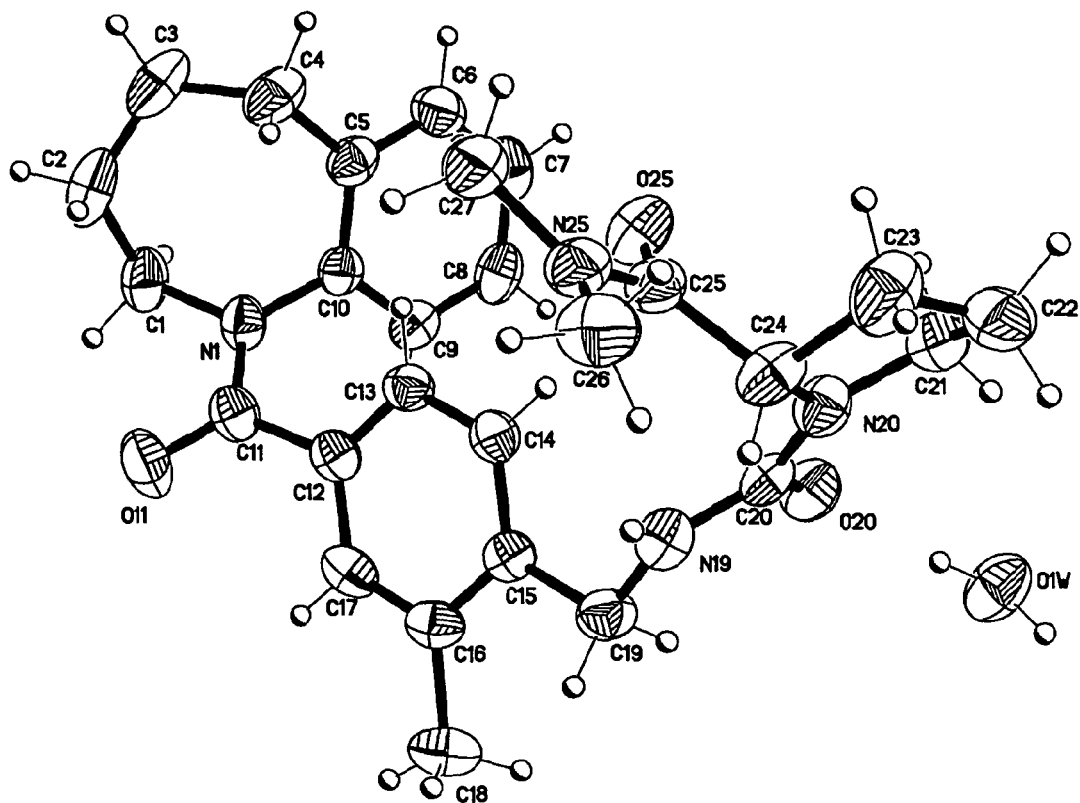

The crystalline form has been isolated as a single crystal and subjected to X-ray crystal structure determination. The result is shown in FIG. 11. As well as confirming the structure of the title compound, the X-ray data show that the crystal lattice contains one molecule of water per molecule of active substance, i.e. the crystalline form of the present invention may exist as a hydrate, particularly a monohydrate.

Thus, in accordance with the present invention, there is provided a crystalline polymorph of 1-(2-methyl-4-(2,3,4,5-tetrahydro-1-benzazepin-1-ylcarbonyl)benzylcarbamoyl)-L-proline-N,N-dimethylamide. In the present application this polymorph may be referred to as 'the crystalline form'.

The name 1-(2-methyl-4-(2,3,4,5-tetrahydro-1-benzazepin-1-ylcarbonyl)benzylcarbamoyl)-L-proline-N,N-dimethylamide denotes the structure depicted in Figure A.

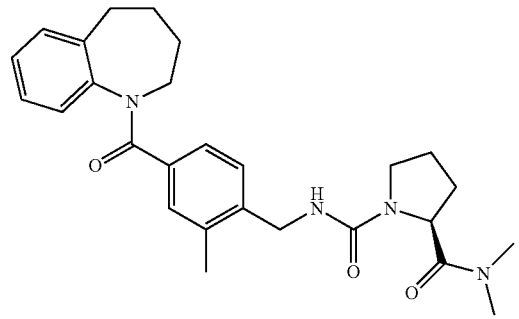

Figure A

The present invention encompasses solvates (e.g. hydrates) of the crystalline form of 1-(2-methyl-4-(2,3,4,5-tetrahydro-1-benzazepin-1-ylcarbonyl)benzylcarbamoyl)-L-proline-N,N-dimethylamide.

In an embodiment, the compound of the invention has crystalline properties and is preferably at least 50%, 60%, 70%, 80% or 90% crystalline. In another embodiment, the compound of the invention is >95% crystalline. Crystallinity can be estimated by conventional X-ray diffractometry techniques or differential scanning calorimetry techniques.

One crystalline polymorph of the compound of the present invention has been isolated and characterised to date, which is herein referred to as 'Form 1'.

In the present specification, X-ray powder diffraction peaks (expressed in degrees 2θ) are measured using copper X-rays with a wavelength of 1.5406 Å (alpha1) and 1.5444 Å (alpha2).

The present invention provides a crystalline form (Form 1) of 1-(2-methyl-4-(2,3,4,5-tetrahydro-1-benzazepin-1-ylcarbonyl)benzylcarbamoyl)-L-proline-N,N-dimethylamide, which exhibits at least the following characteristic X-ray powder diffraction peaks (Cu Kα radiation, expressed in degrees 2θ) at approximately:
(1) 5.5, 10.9, 14.2, 21.9 and 24.0 or
(2) 5.5, 10.6, 10.9, 14.2, 18.8, 21.9 and 24.0 or
(3) 5.5, 10.6, 10.9, 14.2, 15.1, 15.6, 18.8, 21.9 and 24.0.

The term "approximately" means in this context that there is an uncertainty in the measurements of the degrees 2θ of ±0.2 (expressed in degrees 2θ).

The present invention also provides a crystalline form (Form 1) of 1-(2-methyl-4-(2,3,4,5-tetrahydro-1-benzazepin-1-ylcarbonyl)benzylcarbamoyl)-L-proline-N,N-dimethylamide, having an X-ray powder diffraction pattern comprising specific peaks (expressed in degrees 2θ) at approximately 5.5, 10.6, 10.9, 14.2, 15.1, 15.6, 18.8, 21.9, 24.0, 26.0, 26.4 and 26.8.

The present invention also provides a crystalline form (Form 1) of 1-(2-methyl-4-(2,3,4,5-tetrahydro-1-benzazepin-1-ylcarbonyl)benzylcarbamoyl)-L-proline-N,N-dimethylamide, having an X-ray powder diffraction pattern which exhibits at least the following characteristic d-space values (Å) of approximately:
(1) 16.14, 8.11, 6.25, 4.72, 4.06 and 3.71 or
(2) 16.14, 8.37, 8.11, 6.25, 4.72, 4.06 and 3.71 or
(3) 16.14, 8.37, 8.11, 6.25, 5.86, 5.69, 4.72, 4.06 and 3.71.

FIG. 1 shows an X-ray powder diffraction pattern of Form 1 of 1-(2-methyl-4-(2,3,4,5-tetrahydro-1-benzazepin-1-ylcarbonyl)benzylcarbamoyl)-L-proline-N,N-dimethylamide. The present invention also provides a provides a crystalline form (Form 1) of 1-(2-methyl-4-(2,3,4,5-tetrahydro-1-benzazepin-1-ylcarbonyl)benzylcarbamoyl)-L-proline-N,N-dimethylamide having an X-ray powder diffraction pattern substantially the same as that shown in FIG. 1.

Figure 3:
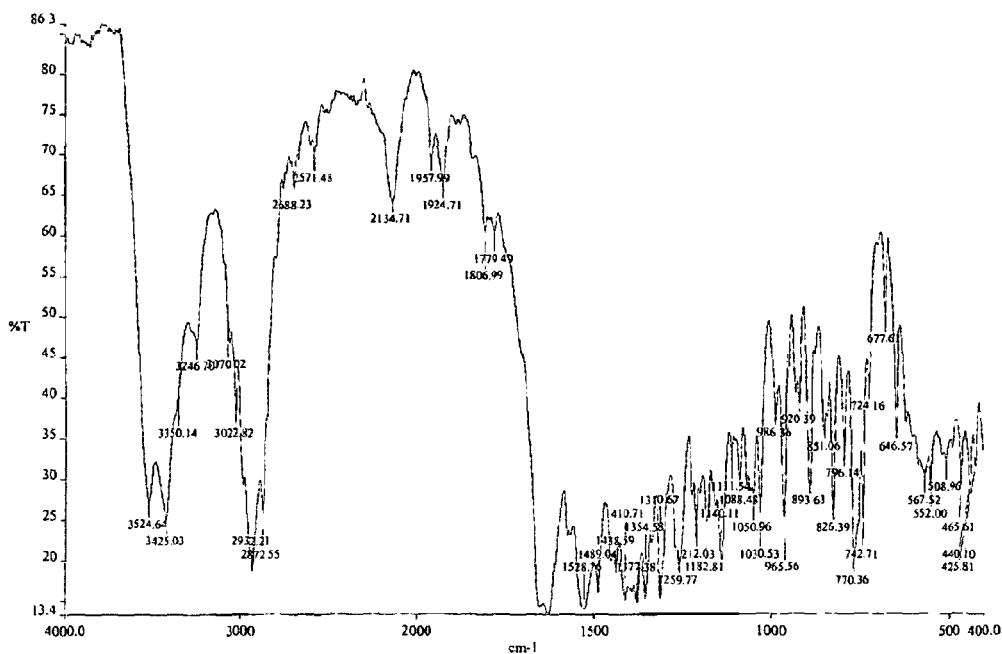

FIG. 3 shows an IR spectrum of Form 1 of 1-(2-methyl-4-(2,3,4,5-tetrahydro-1-benzazepin-1-ylcarbonyl)benzylcarbamoyl)-L-proline-N,N-dimethylamide. The present invention also provides a crystalline form (Form 1) of 1-(2-methyl-4-(2,3,4,5-tetrahydro-1-benzazepin-1-ylcarbonyl)benzylcarbamoyl)-L-proline-N,N-dimethylamide which is characterised by an IR spectrum having characteristic peaks expressed in $cm^{-1}$ at approximately 3525, 3425, 2932, 2873, 2135, 1958, 1925, 1631, 1529, 1489, 1439, 1377, 1355, 1311, 1260, 770, 743.

The term "approximately" means in this context that the $cm^{-1}$ values can vary, e.g. by up to ±1 $cm^{-1}$. Additionally, the present invention provides a crystalline form (Form 1) of 1-(2-methyl-4-(2,3,4,5-tetrahydro-1-benzazepin-1-ylcarbonyl)benzylcarbamoyl)-L-proline-N,N-dimethylamide having an IR spectrum substantially the same as that shown in FIG. 3.

The crystalline form of the present invention can exist in both unsolvated and solvated forms. The term 'solvate' is used herein to describe a molecular complex comprising the compound of the invention and an amount of one or more pharmaceutically acceptable solvents, for example, ethanol. The term 'hydrate' is employed when the solvent is water.

The present invention also encompasses a process for the preparation of the crystalline form of the present invention, said process comprising the crystallisation of said crystalline form from a solution of 1-(2-Methyl-4-(2,3,4,5-tetrahydro-1-benzazepin-1-ylcarbonyl)benzylcarbamoyl)-L-proline-N,N-dimethylamide (prepared using the method described in PCT/GB2001/000023) in a solvent comprising water. In an aspect of the invention, the solvent is water.

The processes of the present invention may also comprise the addition of crystalline seeds of the crystalline form of the invention.

In an aspect, the present invention provides a crystalline form of the invention when manufactured by a process according to the invention.

As previously mentioned, the crystalline form of the present invention has a number of therapeutic applications, particularly in the treatment of diseases or conditions mediated by vasopressin $V_2$.

Accordingly, the present invention provides a crystalline form of 1-(2-methyl-4-(2,3,4,5-tetrahydro-1-benzazepin-1-ylcarbonyl)benzylcarbamoyl)-L-proline-N,N-dimethylamide, or a pharmaceutically acceptable solvate thereof, as hereinbefore defined, for use in therapy.

The present invention also provides for the use of a crystalline form of 1-(2-methyl-4-(2,3,4,5-tetrahydro-1-benzazepin-1-ylcarbonyl)benzylcarbamoyl)-L-proline-N,N-dimethylamide, or a pharmaceutically acceptable solvate thereof, as hereinbefore defined, in the manufacture of a medicament for the treatment of a disease or condition mediated by vasopressin $V_2$ receptors.

The present invention also provides a crystalline form of 1-(2-methyl-4-(2,3,4,5-tetrahydro-1-benzazepin-1-ylcarbonyl)benzylcarbamoyl)-L-proline-N,N-dimethylamide, or a pharmaceutically acceptable solvate thereof, as hereinbefore defined, for use in the treatment of a disease or condition mediated by vasopressin $V_2$ receptors.

The present invention also provides a method of treatment of a disease or condition mediated by vasopressin $V_2$ receptors, said method comprising administering to a mammal in need of such treatment a therapeutically effective amount of a crystalline form of 1-(2-methyl-4-(2,3,4,5-tetrahydro-1-benzazepin-1-ylcarbonyl)benzylcarbamoyl)-L-proline-N,N-dimethylamide, or a pharmaceutically acceptable solvate thereof, as hereinbefore defined.

In an aspect, the disease or condition mediated by vasopressin $V_2$ receptors is selected from nocturnal enuresis, nocturia, polyuria resulting from central diabetes insipidus, urinary incontinence and bleeding disorders.

In an aspect, the disease or condition mediated by vasopressin $V_2$ receptors is nocturia.

In the context of the present invention, references herein to "treatment" include references to curative, palliative and prophylactic treatment, unless there are specific indications to the contrary. The terms "therapy, "therapeutic" and "therapeutically" should be construed in the same way.

The crystalline form of the present invention may be administered alone or in combination with one or more other drugs. Generally, it will be administered as a formulation in association with one or more pharmaceutically acceptable excipients. The term "excipient" is used herein to describe any ingredient other than the compound(s) of the invention which may impart either a functional (i.e., drug release rate controlling) and/or a non-functional (i.e., processing aid or diluent) characteristic to the formulations. The choice of excipient will to a large extent depend on factors such as the particular mode of administration, the effect of the excipient on solubility and stability, and the nature of the dosage form.

Pharmaceutical compositions suitable for the delivery of the crystalline form of the present invention and methods for their preparation will be readily apparent to those skilled in the art. Such compositions and methods for their preparation may be found, for example, in Remington's Pharmaceutical Sciences, 19th Edition (Mack Publishing Company, 1995).

For administration to human patients, the total daily dose of the crystalline form of the invention is typically in the range 0.01 mg and 1000 mg, or between 0.1 mg and 250 mg, or between 1 mg and 50 mg depending, of course, on the mode of administration. The total daily dose may be administered in single or divided doses and may, at the physician's discretion, fall outside of the typical range given herein. These dosages are based on an average human subject having a weight of about 60 kg to 70 kg. The physician will readily be able to determine doses for subjects whose weight falls outside this range, such as infants and the elderly.

Accordingly, the present invention provides a pharmaceutical composition comprising a crystalline solid form of 1-(2-methyl-4-(2,3,4,5-tetrahydro-1-benzazepin-1-ylcarbonyl) benzylcarbamoyl)-L-proline-N,N-dimethylamide, or a pharmaceutically acceptable solvate thereof, as hereinbefore defined, and a pharmaceutically acceptable carrier, diluent or excipient.

The pharmaceutical compositions may be administered topically (e.g. to the skin or to the lung and/or airways) in the form, e.g., of creams, solutions, suspensions, heptafluoroalkane (HFA) aerosols and dry powder formulations; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

In an embodiment of the invention, the active ingredient is administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid plugs, solid microparticulates, semi-solid and liquid (including multiple phases or dispersed systems) such as tablets; soft or hard capsules containing multi- or nano-particulates, liquids, emulsions or powders; lozenges (including liquid-filled); chews; gels; fast dispersing dosage forms; films; ovules; sprays; and buccal/mucoadhesive patches.

Formulations suitable for oral administration may also be designed to deliver the crystalline form in an immediate release manner or in a rate-sustaining manner, wherein the release profile can be delayed, pulsed, controlled, sustained, or delayed and sustained or modified in such a manner which optimises the therapeutic efficacy of the said crystalline form. Means to deliver compounds in a rate-sustaining manner are known in the art and include slow release polymers that can be formulated with the said compounds to control their release.

Examples of rate-sustaining polymers include degradable and non-degradable polymers that can be used to release the said compounds by diffusion or a combination of diffusion and polymer erosion. Examples of rate-sustaining polymers include hydroxypropyl methylcellulose, hydroxypropyl cellulose, methyl cellulose, ethyl cellulose, sodium carboxymethyl cellulose, polyvinyl alcohol, polyvinyl pyrrolidone, xanthum gum, polymethacrylates, polyethylene oxide and polyethylene glycol.

Liquid (including multiple phases and dispersed systems) formulations include emulsions, suspensions, solutions, syrups and elixirs. Such formulations may be presented as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The crystalline form of the invention may also be used in fast-dissolving, fast-disintegrating dosage forms such as those described in Liang and Chen, Expert Opinion in Therapeutic Patents, 2001, 11 (6), 981-986.

The formulation of tablets is discussed in Pharmaceutical Dosage Forms: Tablets, Vol. 1, by H. Lieberman and L. Lachman (Marcel Dekker, New York, 1980).

The invention will now be illustrated by the following non-limiting examples. In the examples the following figures are presented:

FIG. 1: X-ray powder diffraction pattern of Form 1 of 1-(2-methyl-4-(2,3,4,5-tetrahydro-1-benzazepin-1-ylcarbonyl)benzylcarbamoyl)-L-proline-N,N-dimethylamide.

Figure 2:
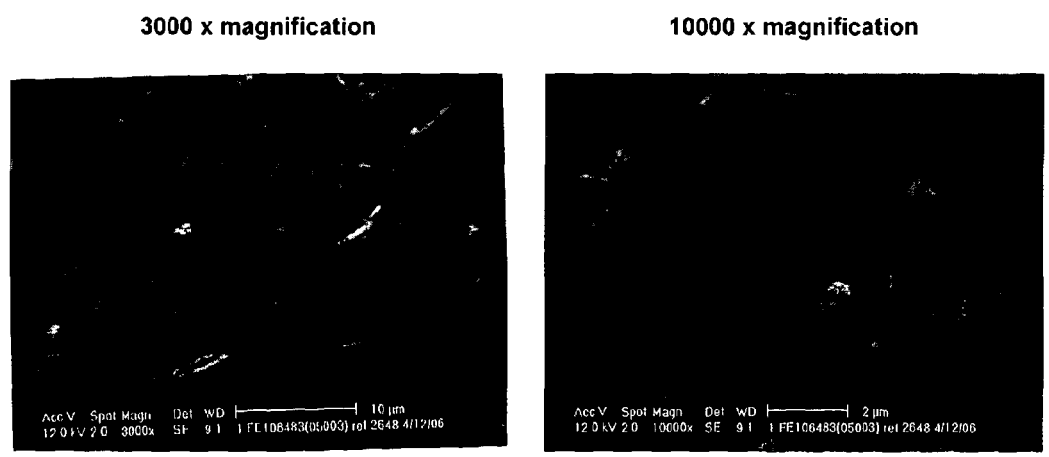

FIG. 2: SEM images of Form 1 of 1-(2-Methyl-4-(2,3,4,5-tetrahydro-1-benzazepin-1-ylcarbonyl)benzylcarbamoyl)-L-proline-N,N-dimethylamide.

FIG. 3: IR spectrum of Form 1 of 1-(2-methyl-4-(2,3,4,5-tetrahydro-1-benzazepin-1-ylcarbonyl)benzylcarbamoyl)-L-proline-N,N-dimethylamide.

Figure 4:
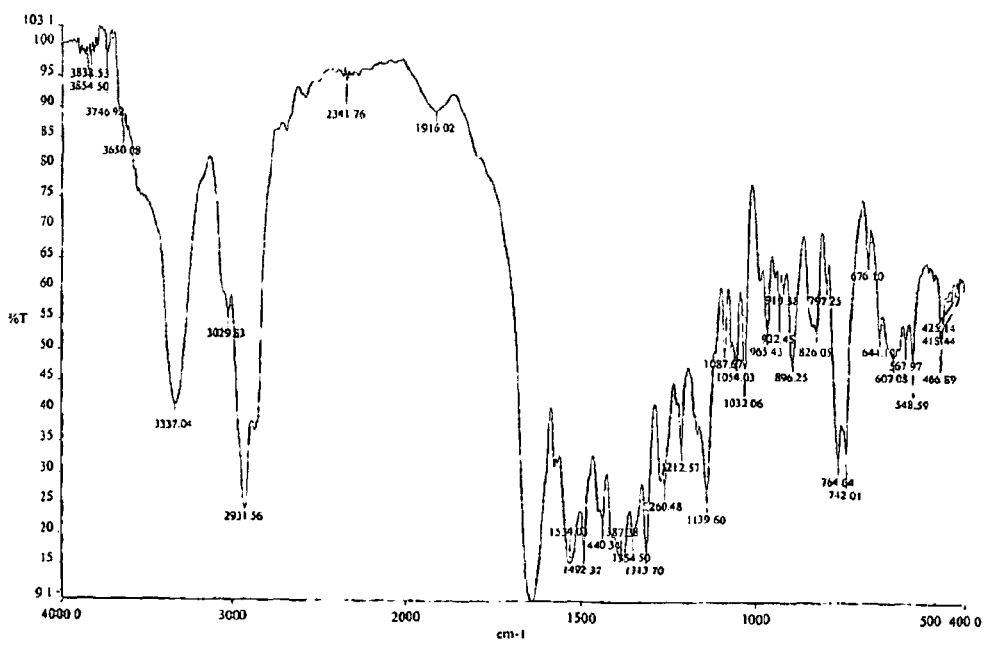

FIG. 4: IR spectrum of amorphous 1-(2-methyl-4-(2,3,4,5-tetrahydro-1-benzazepin-1-ylcarbonyl)benzylcarbamoyl)-L-proline-N,N-dimethylamide.

Figure 5:
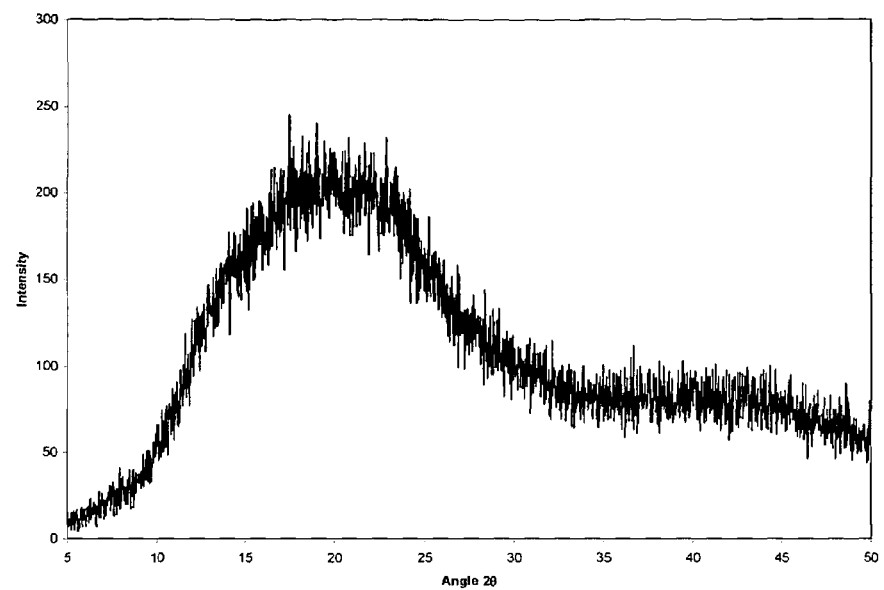

FIG. 5: X-ray powder diffraction pattern of amorphous 1-(2-methyl-4-(2,3,4,5-tetrahydro-1-benzazepin-1-ylcarbonyl)benzylcarbamoyl)-L-proline-N,N-dimethylamide.

Figure 6:
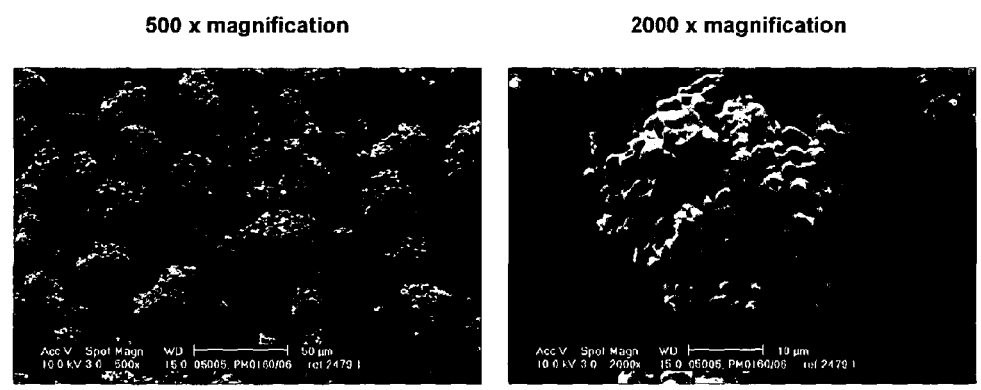

FIG. 6: SEM images of amorphous 1-(2-Methyl-4-(2,3,4,5-tetrahydro-1-benzazepin-1-ylcarbonyl)benzylcarbamoyl)-L-proline-N,N-dimethylamide.

FIG. 7: GVA water sorption/desorption isotherm of amorphous 1-(2-Methyl-4-(2,3,4,5-tetrahydro-1-benzazepin-1-ylcarbonyl)benzylcarbamoyl)-L-proline-N,N-dimethylamide.

FIG. 8: GVA kinetic water sorption/desorption isotherm of amorphous 1-(2-Methyl-4-(2,3,4,5-tetrahydro-1-benzazepin-1-ylcarbonyl)benzylcarbamoyl)-L-proline-N,N-dimethylamide.

FIG. 9: GVA water sorption/desorption isotherm of Form 1 of 1-(2-Methyl-4-(2,3,4,5-tetrahydro-1-benzazepin-1-ylcarbonyl)benzylcarbamoyl)-L-proline-N,N-dimethylamide.

FIG. 10: GVA kinetic water sorption/desorption isotherm of Form 1 of 1-(2-Methyl-4-(2,3,4,5-tetrahydro-1-benzazepin-1-ylcarbonyl)benzylcarbamoyl)-L-proline-N,N-dimethylamide.

FIG. 11: Single crystal X-ray structure of Form 1 of 1-(2-methyl-4-(2,3,4,5-tetrahydro-1-benzazepin-1-ylcarbonyl) benzylcarbamoyl)-L-proline-N,N-dimethylamide.

Figure 12:
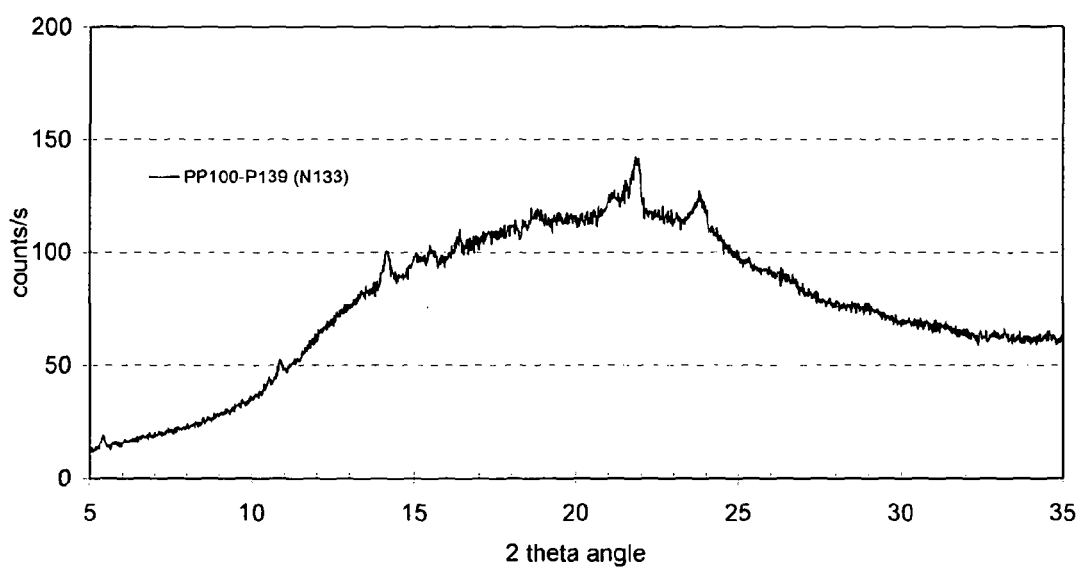

FIG. 12: X-ray powder diffraction pattern of a mixture of 95% amorphous 1-(2-methyl-4-(2,3,4,5-tetrahydro-1-benzazepin-1-ylcarbonyl)benzylcarbamoyl)-L-proline-N,N-dimethylamide and 5% Form 1 of 1-(2-methyl-4-(2,3,4,5-tetrahydro-1-benzazepin-1-ylcarbonyl)benzylcarbamoyl)-L-proline-N,N-dimethylamide.

GENERAL EXPERIMENTAL DETAILS

All solvents and commercial reagents were used as received.

Karl Fischer moisture content determination was carried out using Metrohm 795 KFT volumetric Karl Fischer apparatus. Sample size was approximately 100 mg and the determination was carried out in duplicate.

Gravimetric Vapour Sorption Analysis (GVA) was carried out with approximately 20 mg of sample placed into a suitable sample holder such as a wire-mesh vapour sorption balance pan. This was loaded into either an IGAsorp (Hiden Analytical Instruments) or a DVS Intrinsic (Surface Measurement Systems) vapour sorption balance held at 25+/−0.1° C. The sample was then dried by maintaining a 0% humidity environment until no further weight change was recorded (alternatively, the sorption/desorption cycle is initiated at typical ambient conditions of 40% relative humidity). Subsequently, the sample was then subjected to a ramping profile up to 90% relative humidity at 10% relative humidity increments, maintaining the sample at each step until equilibration had been attained (99.5% step completion). Upon reaching equilibration, the relative humidity within the apparatus was ramped to the next step and the equilibration procedure repeated. After completion of the sorption cycle, the sample was then dried using the same procedure. The weight change during the sorption/desorption cycles was then monitored, allowing for the hygroscopic nature of the sample to be determined.

HPLC data were collected using a Zorbax Extend C18, 2.1 mm×150 mm, 5 μm d.p. column. Flow rate was 0.3 mL/min. Injection volume was 10 μL, detector wavelength 220 nm and column temperature 40° C. Eluent A was 10 mM aqueous ammonium acetate, pH 5.0. Eluent B was 20:80 v/v 10 mM aqueous ammonium acetate: acetonitrile. The gradient programme is shown below:

| Time (min) | Eluent A (%) | Eluent B (%) |
|---|---|---|
| 0.00 | 61.0 | 39.0 |
| 8.00 | 57.0 | 43.0 |
| 12.00 | 30.0 | 70.0 |
| 22.00 | 30.0 | 70.0 |
| 23.00 | 61.0 | 39.0 |
| 35.00 | 61.0 | 39.0 |

Differential Scanning Calorimetry (DSC):

Approximately 1 to 3 mg of the sample was accurately weighed into an aluminium DSC pan and sealed using a non-hermetic lid. Subsequently, the sample was loaded into a Mettler 12E DSC Instrument equipped with a Julabo F25 cooling unit. The samples were heated from 50 to 200° C. at 10° C./min and the change in heat-flow response monitored. The instrument had been previously calibrated using a twin point calibration of indium and lead reference standards as required.

Hyper differential scanning calorimetry: Approximately 1 to 3 mg of the sample was accurately weighed into an aluminium DSC pan and sealed using a non-hermetic lid. Subsequently, the sample was loaded into a Diamond DSC (Perkin-Elmer Instruments, US) equipped with a liquid nitrogen cooling unit and cooled to 0° C. Once a stable baseline had been attained, the samples were heated from 0 to 200° C. at 200° C./min and the change in heat-flow response monitored. A helium purge gas was used at a flow rate of 20 ml/min in order to improve the heat transfer process from the sample to the thermocouples and ultimately improve sensitivity. Prior to analysis the instrument was temperature and heat-flow calibrated using an indium reference standard.

Infra-red spectra were measured using a system set to a Diffuse Reflectance configuration, with samples prepared with potassium bromide, and scanned from 4000 cm$^{-1}$ to 400 cm$^{-1}$.

X-Ray Powder Diffraction (XRPD) patterns were collected using sample weights of approximately 2-10 mg, which was gently compressed on the XRPD zero background single obliquely cut silica sample holder. The sample was then loaded into a Philips X-Pert MPD diffractometer and analysed using the following experimental conditions:—
  Tube anode: Cu
  Generator tension: 40 kV
  Tube current: 40 mA
  Wavelength alpha1: 1.5406 Å
  Wavelength alpha2: 1.5444 Å
  Start angle [2 θ]: 5
  End angle [2 θ]: 50
  Time per step: 2.5 seconds (X-Pert MPD) or 31 seconds (X-Pert Pro).

Scanning electron micrographs were produced by coating the desired material with a thin layer of gold (sputter coating) and examined using a FEI-Philips XL30 Scanning S electron microscope. The acceleration voltage of the electrons used for analysis was 10 KV. All images were captured with a computer controlled CCD camera attachment.

Raman microscopy was carried out using a BWTEK BTR-111 miniature Raman spectrometer using a 785 nm excitation wavelength and measuring data from 3000 cm$^{-1}$ to 100 cm$^{-1}$.

1-(2-methyl-4-(2,3,4,5-tetrahydro-1-benzazepin-1-ylcarbonyl)benzylcarbamoyl)-L-proline-N,N-dimethylamide (Form 1)

Method A 1-(2-Methyl-4-(2,3,4,5-tetrahydro-1-benzazepin-1-ylcarbonyl)benzylcarbamoyl)-L-proline-N,N-dimethylamide (15.0 g; prepared using the method described in PCT/GB2001/000023) was suspended in water (1000 mL) and stirred for 12 days. The mixture was filtered and the solid washed with ice-cold water. The solid was dried at 60° C. to constant weight to afford the crystalline solid form as a white powder.

Method B 1-(2-Methyl-4-(2,3,4,5-tetrahydro-1-benzazepin-1-ylcarbonyl)benzylcarbamoyl)-L-proline-N,N-dimethylamide (300 mg; prepared using the method described in PCT/GB2001/000023) was suspended in acetone/water 20/80 (1 mL) and heated to 50° C. to give an emulsion. The mixture was cooled to 30° C. and stirred to give an opaque solution at 30° C. The temperature was reduced to 28° C. to give a clear solution. Stirring was continued for 18 hours to give a suspension and stirred for an additional 30 hours. The solids were removed by filtration, washed with acetone/water 20/80, air dried for 10 minutes and dried further in dessicator for 1 hour to afford the crystalline solid form as a white powder (76% yield).

Method C 1-(2-Methyl-4-(2,3,4,5-tetrahydro-1-benzazepin-1-ylcarbonyl)benzylcarbamoyl)-L-proline-N,N-dimethylamide (200 g; prepared using the method described in PCT/GB2001/000023) was added to a mixture of acetone/water (20/80) (500 mL) and stirred at 15° C. for 5 minutes. The mixture was heated to 50° C. over 15 minutes to give an emulsion, stirred at 50° C. for 10 minutes and cooled to 27° C. over 38 minutes to give a clear solution. A "cloud point" was noted at approximately 38° C. during cooling. Seeds of the crystalline 1-(2-methyl-4-(2,3,4,5-tetrahydro-1-benzazepin-1-ylcarbonyl)benzylcarbamoyl)-L-proline-N,N-dimethylamide (Form 1) (10 g) were suspended in a mixture of acetone/water (20/80) (25 mL) and added to the reaction mixture. A further amount of acetone/water (20/80) (25 mL) was used to rinse residual seed suspension into the mixture. The suspension was left to stir at 27° C. until the total experiment time reached 46 hours. The suspension was cooled to 20° C. over 1 hour and was stirred for a further 42 hours at 20° C. The suspension was filtered and the solids air dried for approximately 30 minutes. The solids were washed with mixtures of acetone/water (5/95, 3×100 mL) and air dried for approximately 3 hours. The solids were dried further at 45° C. in vacuo to afford the crystalline solid form as a white powder, yield 166 g (76%).

An XRPD diffractogram of 1-(2-methyl-4-(2,3,4,5-tetrahydro-1-benzazepin-1-ylcarbonyl)benzylcarbamoyl)-L-proline-N,N-dimethylamide (Form 1) is shown in FIG. 1.
Peak Position Table:

| Pos. [°2Th.] | Height [cts] | FWHM [°2Th.] | d-spacing [Å] | Rel. Int. [%] |
|---|---|---|---|---|
| 5.4754 | 52.82 | 0.1968 | 16.14063 | 3.95 |
| 10.5691 | 141.1 | 0.1574 | 8.37046 | 8.44 |
| 10.9029 | 156.56 | 0.1968 | 8.11496 | 11.71 |
| 12.2633 | 74.39 | 0.2755 | 7.2176 | 7.79 |
| 14.1671 | 526.77 | 0.2362 | 6.2517 | 47.29 |
| 15.1107 | 354.54 | 0.2755 | 5.86334 | 37.13 |
| 15.5663 | 308.05 | 0.2165 | 5.69277 | 25.35 |
| 16.3567 | 118.47 | 0.2755 | 5.4194 | 12.41 |
| 18.0376 | 92.63 | 0.2952 | 4.91799 | 10.39 |
| 18.8113 | 257.21 | 0.433 | 4.71742 | 42.33 |
| 19.517 | 101.18 | 0.2165 | 4.54841 | 8.33 |
| 21.1847 | 351.17 | 0.2362 | 4.19398 | 31.53 |
| 21.5641 | 492.65 | 0.4239 | 4.12103 | 53.65 |
| 21.8694 | 954.78 | 0.2755 | 4.0642 | 100 |
| 23.96 | 600.03 | 0.2558 | 3.7141 | 58.36 |
| 25.9754 | 134.06 | 0.2165 | 3.43033 | 11.03 |
| 26.3607 | 153.56 | 0.1771 | 3.38105 | 10.34 |
| 26.7483 | 157.84 | 0.1968 | 3.33293 | 11.81 |
| 28.5823 | 88.09 | 0.087 | 3.12311 | 1.97 |
| 29.1687 | 142.58 | 0.2755 | 3.06165 | 14.93 |
| 30.5138 | 91.15 | 0.1246 | 2.92967 | 2.92 |
| 30.8276 | 105.54 | 0.1671 | 2.90057 | 4.53 |
| 31.4796 | 66.87 | 0.433 | 2.84196 | 11.01 |
| 32.0522 | 52.67 | 0.2362 | 2.79249 | 4.73 |
| 33.0593 | 49.71 | 0.4723 | 2.70968 | 8.93 |
| 34.6631 | 51.37 | 0.2362 | 2.5879 | 4.61 |
| 35.2115 | 50.8 | 0.2362 | 2.54884 | 4.56 |
| 35.91 | 34.89 | 0.09 | 2.50085 | 0.81 |
| 36.3592 | 67.12 | 0.0542 | 2.47098 | 0.93 |
| 38.0113 | 53.83 | 0.2755 | 2.3673 | 5.64 |
| 39.6353 | 63.12 | 0.087 | 2.27397 | 1.41 |
| 40.0448 | 79.61 | 0.0949 | 2.25165 | 2.91 |
| 40.8189 | 50.25 | 0.2362 | 2.21072 | 4.51 |
| 41.4384 | 50.14 | 0.2362 | 2.17909 | 4.5 |
| 44.6841 | 29.53 | 0.4723 | 2.02806 | 5.3 |
| 48.0156 | 26.93 | 0.576 | 1.89327 | 7.97 |

SEM Analysis:

The SEM images showed that the crystals of Form 1 have rectangular morphology (see FIG. 2). By way of comparison, the SEM images of the amorphous form showed that the samples studied consisted of predominantly large (>5 μm in diameter) aggregates (see FIG. 6).

Infra-red spectroscopy, spectrum comprises peaks at wavelengths of approximately 3524.6, 3425.0, 2932.2, 2872.6, 2134.7, 1958.0, 1924.7, 1630.7, 1528.8, 1489.0, 1438.6, 1377.4, 1354.6, 1310.7, 1259.8, 770.4, 742.7 cm$^{-1}$. The spectrum is presented in FIG. 3.

DSC: onset approximately 109.9° C.

Hyper DSC: onset approximately 114° C.

Karl Fisher analysis indicates a moisture content of 3.8% which is equivalent to a stoichiometric amount of water and consistent with isolation of a hydrate.

Hygroscopicity Testing

The amorphous form is hygroscopic as indicated by Gravimetric Vapour Sorption Analysis (GVA). The water sorption/desorption isotherms are shown in FIGS. 7 and 8.

The GVA revealed that the amorphous form was highly hygroscopic, absorbing water into the bulk of the sample upon storage above 30% RH (total of ca. 14% at equilibration at 90% RH). The amorphous state remained stable to recrystallisation over the entire water sorption range investigated however a degree of physical form change was observed as the sample passed through its glass transition temperature. In contrast, there was no significant water uptake observed between 40% RH and 90% RH (approximately 0.3% w/w) by the crystalline solid form (the water sorption/desorption isotherms are shown in FIGS. 9 and 10). There was no change in solid state form over the entire water sorption range.

Stability Testing

The crystalline solid form is more stable than the amorphous form. When both substances are stored for 6 months at 40° C. and 75% relative humidity, the crystalline form remains as a white powder with no change in water content (3.8% according to Karl Fischer analysis). Also, there is no significant degradation as measured by the sum of impurities which increases only from 0.9% to 1.0% (HPLC). However, the amorphous form showed increased moisture content, 5.7% from 1.3%, according to Karl Fischer analysis. The amorphous form also shows faster degradation with increased amounts of impurities, 3.7% from 1.5% (HPLC). The amorphous form was initially a white powder but became glassy in appearance and became yellow in colour upon storage.

Detection of Small Amounts of Crystalline Form (Form 1) in a Sample of the Amorphous Form XRPD measurements were carried out with a Bruker D8 Advance powder X-ray diffractometer using Cu Kα radiation in the Bragg-Brentano reflection geometry. Generally, the 2θ values are accurate within an error of ±0.1-0.2°. The relative peak intensities can vary considerably for different samples of the same crystalline form because of different preferred orientations of the crystals. The samples were prepared without any special treatment other than the application of slight pressure to get a flat surface. Silicon single crystal sample holders of 1.0 mm depth and 12 mm cavity diameter were used. The tube voltage and current were 40 kV and 40 mA, respectively. The X-ray diffractometer is equipped with a LynxEye detector. A variable divergence slight was used with a 3° window. The step size was 0.02° 2θ with a step time of 37 seconds. The samples were rotated at 0.5 rps during the measurement.

FIG. 12 shows the XRPD pattern of a mixture with 95% amorphous form and 5% crystalline form (Form 1) showing small peaks in the X-ray diffractogram as listed below.

XRPD Peak List in 2θ angle (for the peaks as visible in the FIG. 12).

| Pos. [°2Th.] |
|---|
| 5.4 |
| 10.9 |
| 14.1 |
| 21.9 |
| 23.8 |

In conclusion, a sample should be at least 5% crystalline in order to see significant XRPD peaks with a reasonable signal to noise ratio.

Assessment of the Crystalline Form 1 Fraction by DSC

An approximate assessment of the content of crystalline form compared to amorphous form can be performed by differential scanning calorimetry. Differential Scanning calorimetry (DSC) measurements were carried out on a Perkin Elmer DSC-7. Samples are placed into gold crucibles, the open sample pan is placed under a nitrogen purge for 3 minutes and hermetically sealed under nitrogen. The measurements are performed at a heating rate of 40° C. per minute over the temperature range from −50° C. to 200° C. Sample amounts are generally about 4 mg and peak integration is carried out from about 80° C. to about 130° C.

Samples containing at least 50% crystalline form exhibit an enthalpy of fusion greater than approximately 30 J/g. Samples containing at least 70% crystalline form exhibit an enthalpy of fusion greater than approximately 45 J/g. Samples containing at least 90% crystalline form exhibit an enthalpy of fusion greater than approximately 58 J/g and samples containing at least 95% crystalline form exhibit an enthalpy of fusion greater than about 62 J/g.

Tablet Manufacture

Active substance is passed through a through a U3 Comil® (Quadro Engineering) fitted with a 457 micron mesh and weighed into a stainless steel container. Lactose monohydrate is added and the mixture blended and passed through a 600 micron sieve. Microcrystalline cellulose was passed through a 600 micron sieve, added and blended. Magnesium stearate was passed through a 600 micron sieve, added and blended. Tablet cores are compressed on a suitable tablet press. A suspension of the film coating material, containing hypromellose, talc, titanium dioxide, polyethylene glycol and saccharin sodium is prepared in purified water, and sprayed onto the tablet cores in a fluid bed coater. The water is removed during processing.

Biological Activity

The ability of the crystalline form of the invention to agonise the vasopressin $V_2$ receptor may be determined using the in vivo assay described in PCT/GB2001/000023.

When tested in this assay, 1-(2-Methyl-4-(2,3,4,5-tetrahydro-1-benzazepin-1-ylcarbonyl)benzylcarbamoyl)-L-proline-N,N-dimethylamide showed 82% inhibition of urine output (at 1 hour) when dosed at 1 mg/Kg.

Single Crystal X-Ray Structure Determination.

Preparation of Crystals:

A suspension (15 mL) of amorphous 1-(2-methyl-4-(2,3,4,5-tetrahydro-1-benzazepin-1-ylcarbonyl)benzylcarbamoyl)-L-proline-N,N-dimethylamide (prepared using the method described in PCT/GB2001/000023) at a concentration of 387 mg/mL in a mixture of n-propyl acetate and water (81:19) was prepared and heated at 80° C. for 10 minutes to give an almost clear solution. The mixture was cooled at a rate of 1° C. per minute to 10° C. and heated again to 40° C. Crystalline seeds of 1-(2-methyl-4-(2,3,4,5-tetrahydro-1-benzazepin-1-ylcarbonyl)benzylcarbamoyl)-L-proline-N,N-dimethylamide (Form 1) (approximately 50 mg) were added and the mixture cooled at a rate of 0.5° C. per minute to 38° C. The mixture heated again to 39° C. and an additional amount of crystalline seeds of 1-(2-methyl-4-(2,3,4,5-tetrahydro-1-benzazepin-1-ylcarbonyl)benzylcarbamoyl)-L-proline-N,N-dimethylamide (Form 1) (approximately 50 mg) were added. The mixture was stirred at 39° C. for 6 hours then cooled to 35° C. at a rate of 0.1° C. per minute. The mixture was stirred at 35° C. for 6 hours then cooled to 30° C. at a rate of 0.1° C. per minute. The mixture was then stirred for three days at 30° C. It was observed that the reaction vessel contained a suspension and some relatively large crystals on the sides of the vessel. The suspension was removed and filtered and the resulting filtrate was used to rinse the larger crystals away from the sides of the vessel which were recovered as a suspension. The suspension of the large crystals was stored in a sealed vessel at room temperature for two weeks which resulted in dissolution of the crystals. Further storage of the vessel for an additional 10 days in the sealed vessel resulted in recrystallisation to provide crystals suitable for single crystal X-ray structure determination. DSC and Raman analyses of the filtered crystals showed the solids were consistent with Form 1, with no indication of any other crystalline form being present.

Structure Determination:

Crystallography was carried out using a Nonius Kappa CCD (Bruker) instrument. The absolute structure was assigned from the known configuration of the starting material (L-proline dimethyl amide, see PCT/GB2001/000023). The water hydrogen atoms were located and their positions were refined satisfactorily. 2356 Friedel pairs were averaged for the refinement. The resulting single crystal X-ray structure is shown in FIG. 11. The summary report of the single crystal X-ray structure determination is shown below and in Tables 1-5:—

Unit Cell 7436 reflections with 1.00°<theta<28.70° (resolution between 20.40 A and 0.74 A) were used for unit cell refinement

| Symmetry used in scalepack | p2 |
|---|---|
| a (Angstrom) | 8.0686 +/− 0.0002 |
| b (Angstrom) | 9.6869 +/− 0.0002 |
| c (Angstrom) | 16.0886 +/− 0.0004 |
| alpha (°) | 90.000 |
| beta (°) | 91.2676 +/− 0.0008 |
| gamma (°) | 90.000 |
| Volume (A**3) | 1257.17 +/− 0.05 |
| Mosaicity (°) | 0.446 +/− 0.002 |

Data Collection Summary

| Total number of images collected | 165 |
|---|---|
| Total exposure time | 8.7 hours |
| Data collection exposure time | 8.6 hours |
| Data collection wall-clock time | 8.8 hours |

Experimental Conditions

| Wavelength | 0.71073 A |
|---|---|
| Generator setting | 50 kV 30 mA |

Scans

| Type | Name | # images | Total Rotation | Per frame Rotation | Exposure per frame | Detector distance | Used in scaling |
|---|---|---|---|---|---|---|---|
| cell determination | i01f | 10 | 10.0° phi | 1.000° | 20 seconds | 40.00 mm | No |
| data collection | s01f | 88 | 176.0° phi | 2.000° | 200 seconds | 35.00 mm | Yes |
| data collection | s02f | 19 | 38.0° omega | 2.000° | 200 seconds | 35.00 mm | Yes |

-continued

| Type | Name | # images | Total Rotation | Per frame Rotation | Exposure per frame | Detector distance | Used in scaling |
|---|---|---|---|---|---|---|---|
| data collection | s03f | 14 | 28.0° omega | 2.000° | 200 seconds | 35.00 mm | Yes |
| data collection | s04f | 34 | 68.0° omega | 2.000° | 200 seconds | 35.00 mm | Yes |

Scalepack Scaling
Deleted Observations

| Overload or incomplete profile | 366 |
|---|---|
| Sigma cutoff | 43 |
| High resolution limit | 12 |

Final Data Set

| Scale factor | 10.00 |
|---|---|
| Number of 'full' reflections | 8117 |
| Number of 'partial' reflections | 8770 |
| Total number of integrated reflections | 11976 |
| Total number of unique reflections | 3352 |
| Data completeness | 97.8% |
| Resolution range | 20.40-0.74 A |
| Theta range | 1.00°-28.70° |
| Average Intensity | 389.2 |
| Average Sigma(I) | 10.2 |
| Overall R-merge (linear) | 0.037 |

TABLE 1

Crystal data and structure refinement for pp1001.

| Identification code | pp1001 | |
|---|---|---|
| Empirical formula | C27 H36 N4 O4 | |
| Formula weight | 480.60 | |
| Temperature | 180(2) K | |
| Wavelength | 0.71073 Å | |
| Crystal system | Monoclinic | |
| Space group | P2(1) | |
| Unit cell dimensions | a = 8.0686(2) Å | α = 90°. |
| | b = 9.6869(2) Å | β = 91.268(1)°. |
| | c = 16.0886(4) Å | γ = 90°. |
| Volume | 1257.17(5) Å$^3$ | |
| Z | 2 | |
| Density (calculated) | 1.270 Mg/m$^3$ | |
| Absorption coefficient | 0.086 mm$^{-1}$ | |
| F(000) | 516 | |
| Crystal size | 0.37 × 0.21 × 0.10 mm$^3$ | |
| Theta range for data collection | 4.12 to 28.68°. | |
| Index ranges | −10 <= h <= 10, −11 <= k <= 12, −19 <= l <= 21 | |
| Reflections collected | 11956 | |
| Independent reflections | 3340 [R(int) = 0.0312] | |
| Completeness to theta = 28.68° | 97.5% | |
| Absorption correction | Semi-empirical from equivalents | |
| Max. and min. transmission | 0.998 and 0.901 | |
| Refinement method | Full-matrix least-squares on F$^2$ | |

TABLE 1-continued

Crystal data and structure refinement for pp1001.

| Data/restraints/parameters | 3340/1/325 |
|---|---|
| Goodness-of-fit on F$^2$ | 1.030 |
| Final R indices [I > 2sigma(I)] | R1 = 0.0370, wR2 = 0.0906 |
| R indices (all data) | R1 = 0.0446, wR2 = 0.0942 |
| Absolute structure parameter | 0.5(11) |
| Largest diff. peak and hole | 0.270 and −0.150 e.Å$^{-3}$ |

TABLE 2

Atomic coordinates (×10$^4$) and equivalent isotropic displacement parameters (Å$^2$ × 10$^3$) for pp1001. U(eq) is defined as one third of the trace of the orthogonalized U$^{ij}$ tensor.

| | x | y | z | U(eq) |
|---|---|---|---|---|
| N(1) | 1842 (2) | 6613 (2) | 9131 (1) | 41 (1) |
| C(1) | 349 (3) | 6674 (3) | 9647 (1) | 51 (1) |
| C(2) | −1244 (3) | 6581 (3) | 9126 (2) | 64 (1) |
| C(3) | −1536 (3) | 5193 (4) | 8722 (2) | 62 (1) |
| C(4) | −165 (3) | 4738 (3) | 8137 (1) | 55 (1) |
| C(5) | 1444 (3) | 4303 (2) | 8561 (1) | 41 (1) |
| C(6) | 1983 (3) | 2939 (3) | 8531 (1) | 50 (1) |
| C(7) | 3497 (3) | 2538 (3) | 8870 (1) | 52 (1) |
| C(8) | 4518 (3) | 3496 (3) | 9242 (1) | 48 (1) |
| C(9) | 3992 (2) | 4862 (2) | 9310 (1) | 39 (1) |
| C(10) | 2460 (2) | 5252 (2) | 8980 (1) | 34 (1) |
| O(11) | 2064 (2) | 8934 (2) | 9151 (1) | 62 (1) |
| C(11) | 2557 (3) | 7816 (2) | 8897 (1) | 41 (1) |
| C(12) | 3961 (2) | 7793 (2) | 8298 (1) | 36 (1) |
| C(13) | 3947 (2) | 7015 (2) | 7572 (1) | 36 (1) |
| C(14) | 5167 (2) | 7223 (2) | 6991 (1) | 36 (1) |
| C(15) | 6438 (2) | 8171 (2) | 7129 (1) | 35 (1) |
| C(16) | 6489 (2) | 8934 (2) | 7871 (1) | 38 (1) |
| C(17) | 5231 (3) | 8742 (2) | 8433 (1) | 39 (1) |
| C(18) | 7828 (3) | 9986 (3) | 8052 (2) | 53 (1) |
| N(19) | 7359 (2) | 7861 (2) | 5666 (1) | 41 (1) |
| C(19) | 7749 (2) | 8411 (2) | 6480 (1) | 43 (1) |
| O(20) | 8800 (2) | 5897 (2) | 5912 (1) | 46 (1) |
| C(20) | 7935 (2) | 6612 (2) | 5432 (1) | 36 (1) |
| N(20) | 7529 (2) | 6167 (2) | 4656 (1) | 42 (1) |
| C(21) | 8128 (3) | 4870 (3) | 4323 (1) | 51 (1) |
| C(22) | 8058 (3) | 5130 (3) | 3382 (2) | 61 (1) |
| C(23) | 6563 (3) | 5989 (4) | 3264 (1) | 67 (1) |
| C(24) | 6391 (2) | 6861 (3) | 4076 (1) | 45 (1) |
| O(25) | 4191 (2) | 5861 (2) | 4852 (1) | 53 (1) |
| N(25) | 3492 (2) | 7583 (2) | 3956 (1) | 47 (1) |
| C(25) | 4589 (2) | 6743 (2) | 4342 (1) | 41 (1) |
| C(26) | 3906 (3) | 8581 (3) | 3308 (2) | 59 (1) |
| C(27) | 1721 (3) | 7391 (3) | 4086 (2) | 59 (1) |
| O(1W) | 12061 (2) | 4994 (2) | 6101 (1) | 63 (1) |

TABLE 3

Bond lengths [Å] and angles [°] for pp1001.

| N(1)—C(11) | 1.357 (3) | C(7)—H(7) | 0.9500 |
|---|---|---|---|
| N(1)—C(10) | 1.432 (3) | C(8)—C(9) | 1.395 (3) |
| N(1)—C(1) | 1.479 (2) | C(8)—H(8) | 0.9500 |
| C(1)—C(2) | 1.521 (4) | C(9)—C(10) | 1.387 (3) |
| C(1)—H(1A) | 0.9900 | C(9)—H(9) | 0.9500 |
| C(1)—H(1B) | 0.9900 | O(11)—C(11) | 1.227 (3) |

TABLE 3-continued

Bond lengths [Å] and angles [°] for pp1001.

| | | | |
|---|---|---|---|
| C(2)—C(3) | 1.509 (5) | C(11)—C(12) | 1.503 (3) |
| C(2)—H(2A) | 0.9900 | C(12)—C(13) | 1.390 (3) |
| C(2)—H(2B) | 0.9900 | C(12)—C(17) | 1.390 (3) |
| C(3)—C(4) | 1.534 (3) | C(13)—C(14) | 1.388 (3) |
| C(3)—H(3A) | 0.9900 | C(13)—H(13) | 0.9500 |
| C(3)—H(3B) | 0.9900 | C(14)—C(15) | 1.391 (3) |
| C(4)—C(5) | 1.513 (3) | C(14)—H(14) | 0.9500 |
| C(4)—H(4A) | 0.9900 | C(15)—C(16) | 1.404 (3) |
| C(4)—H(4B) | 0.9900 | C(15)—C(19) | 1.520 (3) |
| C(5)—C(6) | 1.392 (3) | C(16)—C(17) | 1.387 (3) |
| C(5)—C(10) | 1.396 (3) | C(16)—C(18) | 1.509 (3) |
| C(6)—C(7) | 1.383 (3) | C(17)—H(17) | 0.9500 |
| C(6)—H(6) | 0.9500 | C(18)—H(18A) | 0.9800 |
| C(7)—C(8) | 1.370 (4) | C(18)—H(18B) | 0.9800 |
| C(18)—H(18C) | 0.9800 | C(2)—C(1)—H(1A) | 109.2 |
| N(19)—C(20) | 1.353 (3) | N(1)—C(1)—H(1B) | 109.2 |
| N(19)—C(19) | 1.443 (3) | C(2)—C(1)—H(1B) | 109.2 |
| N(19)—H(19) | 0.8800 | H(1A)—C(1)—H(1B) | 107.9 |
| C(19)—H(19A) | 0.9900 | C(3)—C(2)—C(1) | 114.3 (2) |
| C(19)—H(19B) | 0.9900 | C(3)—C(2)—H(2A) | 108.7 |
| O(20)—C(20) | 1.241 (2) | C(1)—C(2)—H(2A) | 108.7 |
| C(20)—N(20) | 1.355 (3) | C(3)—C(2)—H(2B) | 108.7 |
| N(20)—C(21) | 1.453 (3) | C(1)—C(2)—H(2B) | 108.7 |
| N(20)—C(24) | 1.459 (3) | H(2A)—C(2)—H(2B) | 107.6 |
| C(21)—C(22) | 1.534 (3) | C(2)—C(3)—C(4) | 114.4 (2) |
| C(21)—H(21A) | 0.9900 | C(2)—C(3)—H(3A) | 108.7 |
| C(21)—H(21B) | 0.9900 | C(4)—C(3)—H(3A) | 108.7 |
| C(22)—C(23) | 1.474 (4) | C(2)—C(3)—H(3B) | 108.7 |
| C(22)—H(22A) | 0.9900 | C(4)—C(3)—H(3B) | 108.7 |
| C(22)—H(22B) | 0.9900 | H(3A)—C(3)—H(3B) | 107.6 |
| C(23)—C(24) | 1.565 (3) | C(5)—C(4)—C(3) | 115.21 (18) |
| C(23)—H(23A) | 0.9900 | C(5)—C(4)—H(4A) | 108.5 |
| C(23)—H(23B) | 0.9900 | C(3)—C(4)—H(4A) | 108.5 |
| C(24)—C(25) | 1.529 (3) | C(5)—C(4)—H(4B) | 108.5 |
| C(24)—H(24) | 1.0000 | C(3)—C(4)—H(4B) | 108.5 |
| O(25)—C(25) | 1.232 (3) | H(4A)—C(4)—H(4B) | 107.5 |
| N(25)—C(25) | 1.344 (3) | C(6)—C(5)—C(10) | 117.51 (19) |
| N(25)—C(27) | 1.461 (3) | C(6)—C(5)—C(4) | 120.9 (2) |
| N(25)—C(26) | 1.466 (3) | C(10)—C(5)—C(4) | 121.6 (2) |
| C(26)—H(26A) | 0.9800 | C(7)—C(6)—C(5) | 121.8 (2) |
| C(26)—H(26B) | 0.9800 | C(7)—C(6)—H(6) | 119.1 |
| C(26)—H(26C) | 0.9800 | C(5)—C(6)—H(6) | 119.1 |
| C(27)—H(27A) | 0.9800 | C(8)—C(7)—C(6) | 120.0 (2) |
| C(27)—H(27B) | 0.9800 | C(8)—C(7)—H(7) | 120.0 |
| C(27)—H(27C) | 0.9800 | C(6)—C(7)—H(7) | 120.0 |
| O(1W)—H(1W) | 0.91 (4) | C(7)—C(8)—C(9) | 119.73 (19) |
| O(1W)—H(2W) | 1.01 (4) | C(7)—C(8)—H(8) | 120.1 |
| C(11)—N(1)—C(10) | 126.28 (15) | C(9)—C(8)—H(8) | 120.1 |
| C(11)—N(1)—C(1) | 118.54 (18) | C(10)—C(9)—C(8) | 119.9 (2) |
| C(10)—N(1)—C(1) | 115.00 (17) | C(10)—C(9)—H(9) | 120.0 |
| N(1)—C(1)—C(2) | 112.17 (17) | C(8)—C(9)—H(9) | 120.0 |
| N(1)—C(1)—H(1A) | 109.2 | C(9)—C(10)—C(5) | 120.93 (19) |
| C(9)—C(10)—N(1) | 119.84 (18) | O(20)—C(20)—N(19) | 121.25 (18) |
| C(5)—C(10)—N(1) | 119.01 (17) | O(20)—C(20)—N(20) | 121.2 (2) |
| O(11)—C(11)—N(1) | 121.55 (17) | N(19)—C(20)—N(20) | 117.58 (18) |
| O(11)—C(11)—C(12) | 118.7 (2) | C(20)—N(20)—C(21) | 122.67 (18) |
| N(1)—C(11)—C(12) | 119.70 (17) | C(20)—N(20)—C(24) | 125.37 (19) |
| C(13)—C(12)—C(17) | 118.82 (17) | C(21)—N(20)—C(24) | 111.87 (17) |
| C(13)—C(12)—C(11) | 123.67 (17) | N(20)—C(21)—C(22) | 102.5 (2) |
| C(17)—C(12)—C(11) | 116.96 (17) | N(20)—C(21)—H(21A) | 111.3 |
| C(14)—C(13)—C(12) | 119.69 (17) | C(22)—C(21)—H(21A) | 111.3 |
| C(14)—C(13)—H(13) | 120.2 | N(20)—C(21)—H(21B) | 111.3 |
| C(12)—C(13)—H(13) | 120.2 | C(22)—C(21)—H(21B) | 111.3 |
| C(13)—C(14)—C(15) | 121.30 (17) | H(21A)—C(21)—H(21B) | 109.2 |
| C(13)—C(14)—H(14) | 119.3 | C(23)—C(22)—C(21) | 103.4 (2) |
| C(15)—C(14)—H(14) | 119.3 | C(23)—C(22)—H(22A) | 111.1 |
| C(14)—C(15)—C(16) | 119.42 (17) | C(21)—C(22)—H(22A) | 111.1 |
| C(14)—C(15)—C(19) | 120.87 (17) | C(23)—C(22)—H(22B) | 111.1 |
| C(16)—C(15)—C(19) | 119.70 (17) | C(21)—C(22)—H(22B) | 111.1 |
| C(17)—C(16)—C(15) | 118.42 (17) | H(22A)—C(22)—H(22B) | 109.0 |
| C(17)—C(16)—C(18) | 119.70 (18) | C(22)—C(23)—C(24) | 106.52 (18) |
| C(15)—C(16)—C(18) | 121.84 (18) | C(22)—C(23)—H(23A) | 110.4 |
| C(16)—C(17)—C(12) | 122.31 (17) | C(24)—C(23)—H(23A) | 110.4 |
| C(16)—C(17)—H(17) | 118.8 | C(22)—C(23)—H(23B) | 110.4 |
| C(12)—C(17)—H(17) | 118.8 | C(24)—C(23)—H(23B) | 110.4 |
| C(16)—C(18)—H(18A) | 109.5 | H(23A)—C(23)—H(23B) | 108.6 |
| C(16)—C(18)—H(18B) | 109.5 | N(20)—C(24)—C(25) | 112.07 (16) |
| H(18A)—C(18)—H(18B) | 109.5 | N(20)—C(24)—C(23) | 102.64 (19) |

TABLE 3-continued

Bond lengths [Å] and angles [°] for pp1001.

| | | | |
|---|---|---|---|
| C(16)—C(18)—H(18C) | 109.5 | C(25)—C(24)—C(23) | 107.18 (17) |
| H(18A)—C(18)—H(18C) | 109.5 | N(20)—C(24)—H(24) | 111.5 |
| H(18B)—C(18)—H(18C) | 109.5 | C(25)—C(24)—H(24) | 111.5 |
| C(20)—N(19)—C(19) | 120.87 (17) | C(23)—C(24)—H(24) | 111.5 |
| C(20)—N(19)—H(19) | 119.6 | C(25)—N(25)—C(27) | 119.5 (2) |
| C(19)—N(19)—H(19) | 119.6 | C(25)—N(25)—C(26) | 124.76 (18) |
| N(19)—C(19)—C(15) | 115.21 (16) | C(27)—N(25)—C(26) | 115.14 (19) |
| N(19)—C(19)—H(19A) | 108.5 | O(25)—C(25)—N(25) | 123.31 (18) |
| C(15)—C(19)—H(19A) | 108.5 | O(25)—C(25)—C(24) | 120.10 (18) |
| N(19)—C(19)—H(19B) | 108.5 | N(25)—C(25)—C(24) | 116.47 (18) |
| C(15)—C(19)—H(19B) | 108.5 | N(25)—C(26)—H(26A) | 109.5 |
| H(19A)—C(19)—H(19B) | 107.5 | N(25)—C(26)—H(26B) | 109.5 |
| H(26A)—C(26)—H(26B) | 109.5 | H(27A)—C(27)—H(27B) | 109.5 |
| N(25)—C(26)—H(26C) | 109.5 | N(25)—C(27)—H(27C) | 109.5 |
| H(26A)—C(26)—H(26C) | 109.5 | H(27A)—C(27)—H(27C) | 109.5 |
| H(26B)—C(26)—H(26C) | 109.5 | H(27B)—C(27)—H(27C) | 109.5 |
| N(25)—C(27)—H(27A) | 109.5 | H(1W)—O(1W)—H(2W) | 99 (3) |
| N(25)—C(27)—H(27B) | 109.5 | | |

Symmetry Transformations Used to Generate Equivalent Atoms:

TABLE 4

Anisotropic displacement parameters ($Å^2 \times 10^3$) for pp1001. The anisotropic displacement factor exponent takes the form:
$-2\pi^2[h^2 a^{*2} U^{11} + \ldots + 2 h k a^* b^* U^{12}]$

| | $U^{11}$ | $U^{22}$ | $U^{33}$ | $U^{23}$ | $U^{13}$ | $U^{12}$ |
|---|---|---|---|---|---|---|
| N(1) | 40(1) | 42(1) | 41(1) | 1(1) | 10(1) | 6(1) |
| C(1) | 51(1) | 57(1) | 47(1) | 3(1) | 20(1) | 10(1) |
| C(2) | 41(1) | 88(2) | 61(1) | 19(1) | 15(1) | 23(1) |
| C(3) | 33(1) | 101(2) | 53(1) | 16(2) | 0(1) | 1(1) |
| C(4) | 38(1) | 82(2) | 44(1) | 2(1) | −4(1) | −4(1) |
| C(5) | 36(1) | 53(1) | 34(1) | 1(1) | 5(1) | −4(1) |
| C(6) | 54(1) | 47(1) | 49(1) | −8(1) | 11(1) | −10(1) |
| C(7) | 64(1) | 42(1) | 50(1) | 6(1) | 19(1) | 10(1) |
| C(8) | 41(1) | 60(1) | 43(1) | 13(1) | 6(1) | 12(1) |
| C(9) | 35(1) | 50(1) | 33(1) | 3(1) | 1(1) | −2(1) |
| C(10) | 35(1) | 38(1) | 31(1) | 3(1) | 6(1) | 1(1) |
| O(11) | 76(1) | 42(1) | 68(1) | −6(1) | 25(1) | 10(1) |
| C(11) | 49(1) | 40(1) | 36(1) | −1(1) | 4(1) | 5(1) |
| C(12) | 42(1) | 32(1) | 34(1) | 4(1) | 1(1) | 3(1) |
| C(13) | 37(1) | 32(1) | 39(1) | 1(1) | 0(1) | −2(1) |
| C(14) | 39(1) | 36(1) | 34(1) | −1(1) | 1(1) | 2(1) |
| C(15) | 36(1) | 33(1) | 36(1) | 7(1) | −1(1) | 1(1) |
| C(16) | 44(1) | 32(1) | 38(1) | 7(1) | −8(1) | −4(1) |
| C(17) | 56(1) | 30(1) | 31(1) | 1(1) | −4(1) | 1(1) |
| C(18) | 63(1) | 48(1) | 48(1) | 1(1) | −8(1) | −18(1) |
| N(19) | 41(1) | 47(1) | 37(1) | 9(1) | 3(1) | 2(1) |
| C(19) | 43(1) | 41(1) | 44(1) | 2(1) | 4(1) | −9(1) |
| O(20) | 39(1) | 52(1) | 46(1) | 8(1) | −6(1) | 6(1) |
| C(20) | 27(1) | 46(1) | 36(1) | 7(1) | 3(1) | −4(1) |
| N(20) | 36(1) | 53(1) | 37(1) | 2(1) | 0(1) | 2(1) |
| C(21) | 44(1) | 55(1) | 53(1) | −5(1) | 2(1) | −6(1) |
| C(22) | 59(1) | 73(2) | 51(1) | −18(1) | −1(1) | −14(1) |
| C(23) | 53(1) | 110(2) | 38(1) | −3(1) | 5(1) | −1(1) |
| C(24) | 36(1) | 64(1) | 36(1) | 9(1) | −3(1) | −5(1) |
| O(25) | 41(1) | 65(1) | 54(1) | 12(1) | 6(1) | −1(1) |
| N(25) | 38(1) | 46(1) | 55(1) | −3(1) | −8(1) | −1(1) |
| C(25) | 36(1) | 49(1) | 38(1) | −4(1) | −3(1) | −3(1) |
| C(26) | 57(1) | 51(1) | 67(2) | 10(1) | −13(1) | 0(1) |
| C(27) | 39(1) | 51(1) | 86(2) | −14(1) | −8(1) | 3(1) |
| O(1W) | 43(1) | 69(1) | 76(1) | 19(1) | 0(1) | 5(1) |

TABLE 5

Hydrogen coordinates ($\times 10^4$) and isotropic displacement parameters ($Å^2 \times 10^3$) for pp1001.

| | x | y | z | U(eq) |
|---|---|---|---|---|
| H(1A) | 355 | 7550 | 9964 | 62 |
| H(1B) | 383 | 5904 | 10051 | 62 |
| H(2A) | −2191 | 6792 | 9486 | 76 |
| H(2B) | −1217 | 7295 | 8687 | 76 |
| H(3A) | −2600 | 5225 | 8404 | 75 |
| H(3B) | −1646 | 4489 | 9164 | 75 |
| H(4A) | −585 | 3956 | 7796 | 66 |
| H(4B) | 71 | 5509 | 7753 | 66 |
| H(6) | 1292 | 2266 | 8270 | 59 |
| H(7) | 3829 | 1598 | 8845 | 63 |
| H(8) | 5580 | 3231 | 9453 | 58 |
| H(9) | 4682 | 5524 | 9583 | 47 |
| H(13) | 3106 | 6344 | 7474 | 43 |
| H(14) | 5134 | 6707 | 6488 | 43 |
| H(17) | 5237 | 9277 | 8928 | 47 |
| H(18A) | 7668 | 10385 | 8605 | 80 |
| H(18B) | 7770 | 10720 | 7633 | 80 |
| H(18C) | 8916 | 9538 | 8037 | 80 |
| H(19) | 6738 | 8345 | 5316 | 50 |
| H(19A) | 7933 | 9418 | 6428 | 51 |
| H(19B) | 8803 | 7994 | 6682 | 51 |
| H(21A) | 7401 | 4091 | 4476 | 61 |
| H(21B) | 9275 | 4674 | 4521 | 61 |
| H(22A) | 9060 | 5626 | 3199 | 73 |
| H(22B) | 7954 | 4252 | 3070 | 73 |
| H(23A) | 5573 | 5399 | 3172 | 80 |
| H(23B) | 6680 | 6602 | 2776 | 80 |
| H(24) | 6718 | 7845 | 3987 | 54 |
| H(26A) | 5024 | 8942 | 3415 | 88 |
| H(26B) | 3107 | 9343 | 3311 | 88 |
| H(26C) | 3862 | 8125 | 2764 | 88 |
| H(27A) | 1563 | 6831 | 4586 | 88 |
| H(27B) | 1219 | 6921 | 3604 | 88 |
| H(27C) | 1192 | 8293 | 4157 | 88 |
| H(1W) | 11040 (50) | 5370 (40) | 6000 (20) | 94 |
| H(2W) | 12680 (50) | 5470 (40) | 5650 (20) | 94 |

The invention claimed is:

1. A solid form of 1-(2-methyl-4-(2,3,4,5-tetrahydro-1-benzazepin-1-ylcarbonyl)benzylcarbamoyl)-L-proline-N,N-dimethylamide, which exhibits at least the following characteristic X-ray powder diffraction peaks (Cu Kα radiation, expressed in degrees 2θ) at approximately 5.5, 10.9, 14.2, 21.9 and 24.0.

2. The solid form according to claim 1 which is characterized by an IR spectrum having peaks expressed in cm$^{-1}$ at approximately 3525, 3425, 2932, 2873, 2135, 1958, 1925, 1631, 1529, 1489, 1439, 1377, 1355, 1311, 1260, 770, 743.

3. The solid form according to claim 1 that is a monohydrate.

4. A pharmaceutical composition comprising 1-(2-methyl-4-(2,3,4,5-tetrahydro-1-benzazepin-1-ylcarbonyl)benzylcarbamoyl)-L-proline-N,N-dimethylamide and a pharmaceutically acceptable adjuvant, diluent or carrier, in which the 1-(2-methyl-4-(2,3,4,5-tetrahydro-1-benzazepin-1-ylcarbonyl)benzylcarbamoyl)-L-proline-N,N-dimethylamide in the composition is the solid form of claim 1.

5. A method of treating a disease or condition that is nocturnal enuresis, nocturia, polyuria resulting from central diabetes insipidus, urinary incontinence, or a bleeding disorder, the method comprising administering a solid form according to claim 1 to a patient in need thereof.

6. The method according to claim 5 wherein the disease or condition is nocturia.

7. The solid form according to claim 2 that is a monohydrate.

8. A pharmaceutical composition comprising 1-(2-methyl-4-(2,3,4,5-tetrahydro-1-benzazepin-1-ylcarbonyl)benzylcarbamoyl)-L-proline-N,N-dimethylamide and a pharmaceutically acceptable adjuvant, diluent or carrier, in which the 1-(2-methyl-4-(2,3,4,5-tetrahydro-1-benzazepin-1-ylcarbonyl)benzylcarbamoyl)-L-proline-N,N-dimethylamide in the composition is the solid form of claim 2.

9. A method of treating a disease or condition that is nocturnal enuresis, nocturia, polyuria resulting from central diabetes insipidus, urinary incontinence, or a bleeding disorder, the method comprising administering a solid form according to claim 2 to a patient in need thereof.

10. The method according to claim 9 wherein the disease or condition is nocturia.

11. A pharmaceutical composition comprising 1-(2-methyl-4-(2,3,4,5-tetrahydro-1-benzazepin-1-ylcarbonyl)benzylcarbamoyl)-L-proline-N,N-dimethylamide and a pharmaceutically acceptable adjuvant, diluent or carrier, in which the 1-(2-methyl-4-(2,3,4,5-tetrahydro-1-benzazepin-1-ylcarbonyl)benzylcarbamoyl)-L-proline-N,N-dimethylamide in the composition is the solid form of claim 3.

12. A method of treating a disease or condition that is nocturnal enuresis, nocturia, polyuria resulting from central diabetes insipidus, urinary incontinence, or a bleeding disorder, the method comprising administering a solid form according to claim 3 to a patient in need thereof.

13. The method according to claim 12, wherein the disease or condition is nocturia.

\* \* \* \* \*